US009181534B1

(12) United States Patent
Hogrefe et al.

(10) Patent No.: US 9,181,534 B1
(45) Date of Patent: *Nov. 10, 2015

(54) HIGH FIDELITY DNA POLYMERASE COMPOSITIONS AND USES THEREOF

(75) Inventors: Holly Hogrefe, San Deigo, CA (US); Michael Borns, Escondido, CA (US); Joseph A. Sorge, Wilson, WY (US)

(73) Assignee: Agilent Technologies Inc., Santa Clara, CA (US)

( * ) Notice: Subject to any disclaimer, the term of this patent is extended or adjusted under 35 U.S.C. 154(b) by 305 days.

This patent is subject to a terminal disclaimer.

(21) Appl. No.: 10/035,091

(22) Filed: Dec. 21, 2001

(51) Int. Cl.
   C12N 9/12 (2006.01)
   C12P 19/34 (2006.01)

(52) U.S. Cl.
   CPC .................... C12N 9/1252 (2013.01)

(58) Field of Classification Search
   USPC .................. 435/174, 183, 15, 91.1, 446, 196; 530/350
   See application file for complete search history.

(56) References Cited

U.S. PATENT DOCUMENTS

| | | | |
|---|---|---|---|
| 5,436,149 A | 7/1995 | Barnes | 435/194 |
| 5,545,552 A | 8/1996 | Mathur | |
| 5,556,772 A | 9/1996 | Sorge et al. | |
| 5,866,395 A | 2/1999 | Mathur | |
| 5,948,663 A | 9/1999 | Mathur | |
| 6,183,997 B1 * | 2/2001 | Hogrefe | 435/91.2 |
| 6,255,062 B1 | 7/2001 | Campbell et al. | |
| 6,333,183 B1 | 12/2001 | Evans et al. | |
| 6,881,559 B2 * | 4/2005 | Sobek et al. | 435/91.2 |

FOREIGN PATENT DOCUMENTS

| | | | | |
|---|---|---|---|---|
| EP | 1 088 891 A1 | 4/2001 | ............. | C12N 15/55 |
| EP | 1 132 474 A1 | 9/2001 | ............. | C12N 15/52 |
| WO | 01/25483 | 4/2001 | | |
| WO | WO 01/23583 A2 | 4/2001 | ............. | C12N 15/55 |

OTHER PUBLICATIONS

Ngo et al., Computational Complexity, Protein Structure Prediction, and the Levinthal Paradox, in The Protein Folding Problem and Tertiary Structure Prediction, 1994, Merz et al. (ed.), Birkhauser, Boston, MA, pp. 433 and 492-495.*
Evans, S.J. et al., (2000), "Improving dideoxynucleotide-triphosphate utilisation by the hyper-thermophilic DNA polymerase from the archaeon *Pyrococcus furiosus*", *Nucleic Acids Research*, 28(5): 1059-1066.
Komori, K. et al., (2000), "Functional interdependence of DNA polymerizing and 3'→5' exonucleolytic activities in *Pyrococcus furiosus* DNA polymerase I", *Protein Engineering*, 13(1): 41-47.
Kong, H. et al., (1993), "Characterization of a DNA Polymerase from the Hyperthermophile Archaea *Thermococcus litoralis*", *The Journal of Biological Chemistry*, 268(3): 1965-1975.

Lam, W. et al., (1998), "Effects of Mutations on the Partitioning of DNA Substrates between the Polymerase and 3'-5' Exonuclease Sites of DNA Polymerase I (Klenow Fragment)", *Biochemistry*, 37: 1513-1522.
Patel, P.H. et al., (2000), "DNA polymerase active site is highly mutable: Evolutionary consequences", *PNAS*, 97(10): 5095-5100.
Suzuki, M. et al., (1996), "Random mutagenesis of *Thermus aquaticus* DNA polymerase I: Concordance of immutable sites in vivo with the crystal structure", *Proc. Natl. Acad. Sci. USA*, 93: 9670-9675.
Zhu, W., et al., (1994), "Mutagenesis of a highly conserved lysine 340 of the PRD1 DNA polymerase", *Biochim. Biophys. Auta.*, 1219: 260-266.
Böhike, et al., "PCR performance of the B-type DNA polymerase from the thermophilic euryarchaeon *Thermococcus aggregans* Improved by mutations in the Y-GG/A motif", *Nucleic Acids Research*, (2000), 3910-3917.
Mattila, et al.; "Fidelity of DNA synthesis by the *Thermococcus litoralis* DNA polymerase-an extremely heat stable enzyme with proofreading activity"; 1991; *Nucleic Acids Research*; 19(18): 4967-4973.
Gardner, et al.; "Determinants of nucleotide sugar recognition in an archaeon DNA polymerase"; 1999; *Nucleic Acids Research*; 27(12): 2545-2553.
European Search Report dated May 23, 2005.
Non-final office action mailed Jan. 28, 2008 in U.S. Appl. No. 10/208,508.
Non-final office action mailed Jan. 14, 2008 in U.S. Appl. No. 10/079,241.
Edgell, et al., "Gene Duplications in Evolution of Archaeal Family B DNA Polymerases", J. Bacteriol. (1997) vol. 179, pp. 2632-2640.
Hopfner et al., "Crystal Structure of a Thermostable Type B DNA Polymerase from *Thermococcus gorgonarius*", Proc.Natl.Acad.Sci. (1999) vol. 96, pp. 3600-3605.
Abdus Sattar, A.K.M., et al., Functional Consequences and Exonuclease Kinetic Parameters of Point Mutations in Bacteriophage T4 DNA Polymerase, 1996, Biochemistry, vol. 35, pp. 16621-16629.
Blanco, Luis, et al., Mutational Analysis of Bacteriophage omega 29 DNA Polymerase, 1995, Methods of Enzymology, vol. 262, pp. 283-294.
Nishioka, et al., Long and Accurate PCR with a Mixture of KOD DNA Polymerase and its Exonuclease Deficient Mutant Enzyme, 2001, Journal of Biotechnology, vol. 88, pp. 141-149.
Pisani, Francesca, M., et al., Amino Acid Residues Involved in Determining the Processivity of the 3'-5' Exonuclease Activity in a Family B DNA Polymerase from the Thermoacidophilic Archaeon *Sulfolobus solfataricus*, 1998, Biochemistry, vol. 37, pp. 15005-15012.

(Continued)

*Primary Examiner* — Richard Hutson

(57) ABSTRACT

The subject invention relates to compositions comprising an enzyme mixture which comprises a first enzyme and a second enzyme, where the first enzyme comprises a DNA polymerization activity and the second enzyme comprises an 5'-3' exonuclease activity and a reduced DNA polymerization activity. The invention also relates to the above compositions in kit format and methods for high fidelity DNA synthesis using the subject compositions of the invention.

33 Claims, 3 Drawing Sheets

(56) References Cited

OTHER PUBLICATIONS

Shen, Yulong, et al., Invariant Asp-1122 and Asp-1124 are Essential Residues for Polymerization Catalysis of Family D DNA Polymerase from *Pyrococcus horikoshii*, Jul. 20, 2001, Journal of Biological Chemistry, vol. 276, No. 29, pp. 27376-27383.

Truniger, Veronica, et al., A DNA Binding Motif Coordinating Synthesis and Degradation in Proofreading DNA Polymerases, 1996, Embo Journal, vol. 15, No. 13, pp. 3430-3441.

Tuske, Steve, et al., The J-helix of *Escherichia coli* DNA Polymerase I (Klenow Fragment) Regulates Polymerase and 3'-5'-Exonuclease Functions, 2000, Journal of Biological Chemistry, vol. 275, No. 31, pp. 23759-23768.

Office Action issued on Oct. 26, 2012 for U.S. Appl. No. 10/208,508.

Office Action issued on Jan. 21, 2014 for European Application No. 091000097.6.

* cited by examiner

Figure 1. PCR Proofreading Activity Assay
*Pfu* G387P
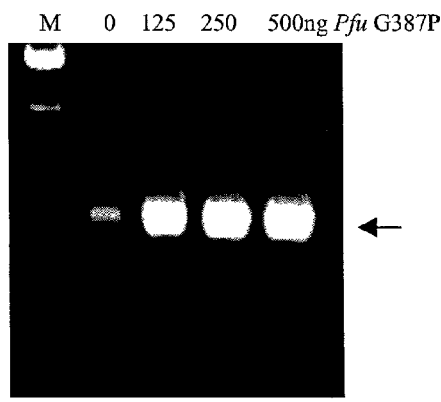
*Pfu* K593T
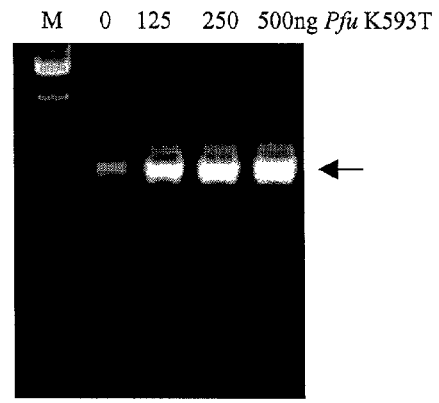

Figure 2. PCR Performance of *Pfu* plus *Pfu* G387P mutant blends
Long genomic targets:
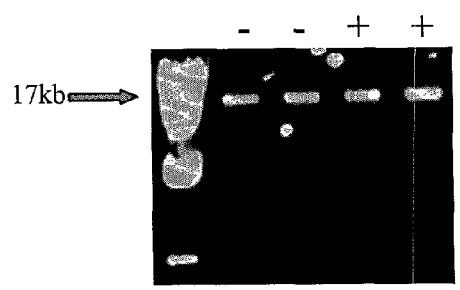
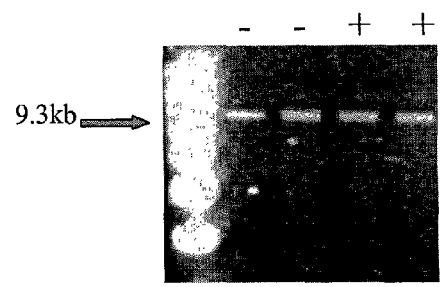
Short/medium genomic targets:
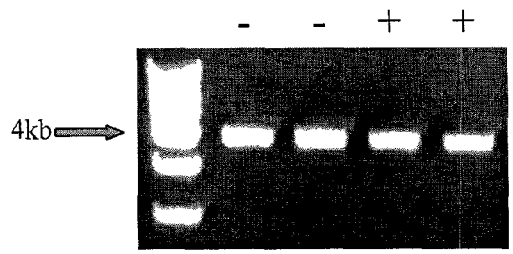
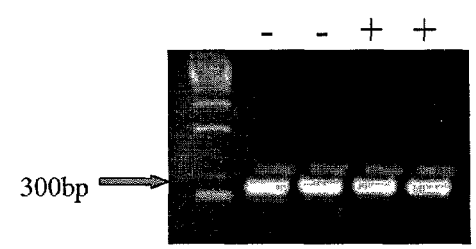

Figure 3. PCR Performance of *Taq* plus *Pfu* G387P mutant blends
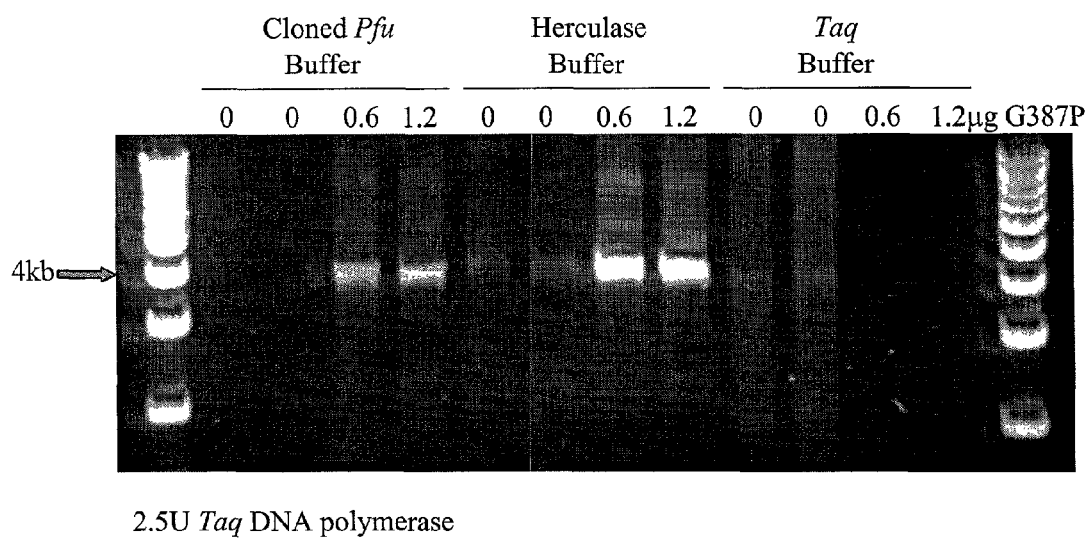
2.5U *Taq* DNA polymerase

HIGH FIDELITY DNA POLYMERASE COMPOSITIONS AND USES THEREOF

FIELD OF THE INVENTION

The present invention is related to the field of high fidelity polynucleotide synthesis.

BACKGROUND OF THE INVENTION

DNA polymerases catalyze the synthesis of DNA and can be found in all cells as well as being encoded in numerous viruses. Although all DNA polymerases possess 5'-3' DNA polymerization activity, DNA polymerases differ from one another in numerous other properties. For example, some enzymatic activities that are possessed by some DNA polymerases, but absent in other DNA polymerases include: double stranded DNA 5'-3' exonuclease activity, single-stranded DNA 3'-5' exonuclease activity, double-stranded 3'-5' DNA exonuclease activity, RNase H activity, reverse transcriptase activity, and the like. Additionally, different DNA polymerases may have different optimal pH and temperature ranges for activity. Furthermore, DNA polymerases may differ in the rate in which they catalyze DNA synthesis.

Purified DNA polymerases have numerous uses in vitro. A detailed description of DNA polymerases, including methods for their isolation, can be found among other places, in *DNA Replication 2nd edition*, by Kornberg and Baker, W. H. Freeman & Company, New York, N.Y. 1991. In vitro uses of DNA polymerases include, for example, the labeling and synthesis of hybridization probes, DNA sequencing, and DNA amplification. A DNA amplification method employing DNA polymerases that has been particularly useful is the polymerase chain reaction (PCR) technique which employs the use of a thermostable DNA polymerase.

The first thermostable DNA polymerase that is widely used for DNA amplification is Taq DNA polymerase isolated from the thermostable, aerobic bacterium *Thermus aquaticus*. Taq DNA polymerase's enzymatic activity at high temperatures allows for primer extension and sequencing of polynucleotide templates with complex secondary structures (i.e., by PCR amplification). However, Taq DNA polymerase has significant error rate when incorporating nucleotides due to the lack of 3'-5' exonuclease activity (i.e., proofreading activity), and therefore may not be suitable if the amplified sequence is to be used in further gene structural/functional studies or cloning.

In the last 10 years, numerous studies have quantified the error rate of thermostable DNA polymerases, and several enzymes have been found to copy DNA more accurately than Taq DNA polymerase (referred to as high fidelity DNA polymerases). U.S. Patent describing DNA polymerases include U.S. Pat. Nos. 4,492,130; 4,946,786; 5,210,036; 5,420,029; 5,489,523; 5,506,137; 5,545,552; 5,618,711; 5,624,833; 6,238,905; 6,100,078; 6,077,664; 5,968,799; 5,948,663; 5,885,713; 5,834,285; 5,756,334; 5,747,298; 5,744,312; 5,624,833; 5,602,011; 5,556,772.

High fidelity polymerases alone should definitely increase fidelity rates but usually do not amplify long fragments as efficient as a DNA polymerase lacking a 3'-5' exonuclease activity (e.g., Taq DNA polymerase). Enzyme mixtures that combine a standard polymerase with a small amount of proofreading polymerase may provide a balance between fidelity and yield. A study published in 1994 illustrated that the use of a high level of a DNA polymerase lacking 3'-5' exonuclease activity (an exo$^-$ DNA polymerase, Klentaq-1) with a very low level of a thermostable DNA polymerase exhibiting 3'-5' exonuclease activity (an exo$^+$ DNA polymerase such as Pfu, Vent, or Deep Vent) generated products with increased base-pair fidelity with a maximum yield of 35 kb DNA from 1 ng of lambda DNA template (Barnes, Proceedings of the National Academy of Sciences, 91:2216-20, 1994). Similarly, U.S. Pat. Nos. 5,436,149 and 6,008,025 disclosed methods for improving DNA amplification fidelity using a DNA polymerase composition comprising a first enzyme substantially lacking 3'-5' exonuclease activity and a second enzyme comprising 3'-5' exonuclease activity. In mixtures such as these, the exo$^+$ enzyme acts to correct polymerization errors produced by the exo$^-$ DNA polymerase.

The problem inherited in the above composition comprising the mix of two DNA polymerase is that the high polymerization activity resulted from combining the two DNA polymerases may inhibit the efficiency and therefore the yield of the amplification reaction. It is also known that the amplification fidelity may also be affected by high DNA polymerase concentration (see for example, Mattila et al., 1991, Polynucleotides Research, 19:4967-73).

There is therefore a need in the art for new methods and compositions which improve polymerization fidelity and reduce the side effects resulted from having high polymerization activity in the reaction.

SUMMARY OF THE INVENTION

The invention provides an enzyme mixture for DNA synthesis comprising a first enzyme and a second enzyme, where the first enzyme comprises a DNA polymerization activity, and the second enzyme comprises a 3'-5' exonuclease activity and a reduced DNA polymerization activity.

In one embodiment, the first enzyme is a DNA polymerase or a reverse transcriptase.

Preferably, the DNA polymerase is selected from the group consisting of: Taq DNA polymerase, Tth DNA polymerase, U1Tma DNA polymerase, Tli DNA polymerase, Pfu DNA polymerase, KOD DNA polymerase, JDF-3 DNA polymerase, Tgo DNA polymerase, PGB-D DNA polymerase and DP1/DP2 DNA polymerase.

Also preferably, the second enzyme is a mutant DNA polymerase.

In one embodiment, the mutant DNA polymerase is derived from a DNA polymerase different from the first enzyme.

The invention also provides an enzyme mixture for DNA synthesis comprising a first enzyme and a second enzyme, where the first enzyme is a wild type Pfu DNA polymerase, the second enzyme is a mutant Pfu DNA polymerase comprising a 3'-5' exonuclease activity and a reduced DNA polymerization activity.

The invention further provides an enzyme mixture for DNA synthesis comprising a first enzyme and a second enzyme, where the first enzyme is a Taq DNA polymerase, the second enzyme is a mutant Pfu DNA polymerase comprising a 3'-5' exonuclease activity and a reduced DNA polymerization activity.

Preferably, the mutant DNA polymerase is derived from a DNA polymerase selected from the group consisting of: U1Tma DNA polymerase, Tli DNA polymerase, Pfu DNA polymerase, KOD DNA polymerase, JDF-3 DNA polymerase, Tgo DNA polymerase, PGB-D DNA polymerase and DP1/DP2 DNA polymerase.

Also preferably, the mutant Pfu DNA polymerase comprises one or more mutations at amino acid positions selected from the group consisting of: D405, Y410, T542, D543, K593, Y595, Y385, G387, and G388.

Still more preferably, the mutant Pfu DNA polymerase comprises one or more mutations selected from the group consisting of: D405E, Y410F, T542P, D543G, K593T, Y595S, Y385Q, Y385S, Y385N, Y385L, Y385H, G387S, G387P, and G388P.

The invention provides a kit for DNA synthesis comprising a first enzyme and a second enzyme, where the first enzyme comprises a DNA polymerization activity, the second enzyme comprises a 3'-5' exonuclease activity and a reduced DNA polymerization activity, and packaging material therefore.

Preferably, the first enzyme in the kit is a DNA polymerase or a reverse transcriptase.

More preferably, the DNA polymerase in the kit is selected from the group consisting of: Taq DNA polymerase, Tth DNA polymerase, U1Tma DNA polymerase, Tli DNA polymerase, Pfu DNA polymerase, KOD DNA polymerase, JDF-3 DNA polymerase, Tgo DNA polymerase, PGB-D DNA polymerase and DP1/DP2 DNA polymerase.

Preferably, the second enzyme in the kit is a mutant DNA polymerase.

More preferably, the mutant DNA polymerase is derived from a DNA polymerase selected from the group consisting of: U1Tma DNA polymerase, Tli DNA polymerase, Pfu DNA polymerase, KOD DNA polymerase, JDF-3 DNA polymerase, Tgo DNA polymerase, PGB-D DNA polymerase and DP1/DP2 DNA polymerase.

Still more preferably, the mutant DNA polymerase is derived from a DNA polymerase different from the first enzyme.

The invention provides a kit comprising an enzyme mixture for DNA synthesis, the kit comprises a first enzyme and a second enzyme, and packaging material therefore, where the first enzyme is a wild type Pfu DNA polymerase, the second enzyme is a mutant Pfu DNA polymerase comprising a 3'-5' exonuclease activity and a reduced DNA polymerization activity.

The invention also provides a kit comprising an enzyme mixture for DNA synthesis, the kit comprises a first enzyme and a second enzyme, and packaging material therefore, where the first enzyme is a Taq DNA polymerase, and packaging material therefore, the second enzyme is a mutant Pfu DNA polymerase comprising a 3'-5' exonuclease activity and a reduced DNA polymerization activity.

The kit of the invention may further comprises one or more components selected from the group consisting of: a deoxynucleotide, a reaction buffer, a PCR enhancing factor and/or additive, a control DNA template and a control primer.

The mutant Pfu DNA polymerase of the kit may comprise one or more mutations at amino acid positions selected from the group consisting of: D405, Y410, T542, D543, K593, Y595, Y385, G387, and G388.

Preferably, the mutant Pfu DNA polymerase comprises one or more mutations selected from the group consisting of: D405E, Y410F, T542P, D543G, K593T, Y595S, Y385Q, Y385S, Y385N, Y385L, Y385H, G387S, G387P, and G388P.

The invention provides a method for DNA synthesis comprising:

(a) providing an enzyme mixture, the enzyme mixture comprising a first enzyme comprising a DNA polymerization activity, and a second enzyme comprising a 3'-5' exonuclease activity and a reduced DNA polymerization activity; and (b) contacting the enzyme mixture with a nucleic acid template, where the enzyme mixture permits DNA synthesis.

Preferably, in the method of the invention, the nucleic acid template is a DNA or an RNA molecule.

Also preferably, the first enzyme used in the method is a DNA polymerase or a reverse transcriptase.

More preferably, the DNA polymerase is selected from the group consisting of Taq DNA polymerase, Tth DNA polymerase, U1Tma DNA polymerase, Tli DNA polymerase, Pfu DNA polymerase, KOD DNA polymerase, JDF-3 DNA polymerase, Tgo DNA polymerase, PGB-D DNA polymerase and DP1/DP2 DNA polymerase.

Also preferably, the second enzyme is a mutant DNA polymerase.

More preferably, the mutant DNA polymerase is derived from a DNA polymerase selected from the group consisting of: U1Tma DNA polymerase, Tli DNA polymerase, Pfu DNA polymerase, KOD DNA polymerase, JDF-3 DNA polymerase, Tgo DNA polymerase, PGB-D DNA polymerase and DP1/DP2 DNA polymerase.

Still more preferably, the mutant DNA polymerase is derived from a DNA polymerase different from the first enzyme.

The invention also provides a method for DNA synthesis comprising:

(a) providing an enzyme mixture, the enzyme mixture comprising a wild type Pfu DNA polymerase as a first enzyme, and a mutant Pfu DNA polymerase as a second enzyme which comprises a 3'-5' exonuclease activity and a reduced DNA polymerization activity; and (b) contacting the enzyme mixture with a nucleic acid template, where the enzyme mixture permits DNA synthesis.

The invention further provides a method for TA cloning of DNA synthesis product comprising:

(a) providing an enzyme mixture, the enzyme mixture comprising a Taq DNA polymerase as a first enzyme, and a mutant Pfu DNA polymerase as a second enzyme which comprises a 3'-5' exonuclease activity and a reduced DNA polymerization activity;

(b) contacting the enzyme mixture with a nucleic acid template, where the enzyme mixture permits DNA synthesis to generate a synthesized DNA product; and (c) inserting the synthesized DNA product into a TA cloning vector.

Preferably, the mutant Pfu DNA polymerase used in the method of the invention comprises one or more mutations at amino acid positions selected from the group consisting of: D405, Y410, T542, D543, K593, Y595, Y385, G387, and G388.

More preferably, the mutant Pfu DNA polymerase comprises one or more mutations selected from the group consisting of: D405E, Y410F, T542P, D543G, K593T, Y595S, Y385Q, Y385S, Y385N, Y385L, Y385H, G387S, G387P, and G388P.

BRIEF DESCRIPTION OF DRAWINGS

FIG. 1. PCR proofreading activity assay using Pfu DNA polymerase mutants according to some embodiments of the invention.

FIG. 2. PCR performance of Pfu plus Pfu G387P mutant blends according to some embodiments of the invention.

FIG. 3. PCR performance of Taq plus Pfu G387P mutant blends according to some embodiments of the invention.

DETAILED DESCRIPTION OF THE INVENTION

The subject invention provides novel composition for high fidelity polynucleotide synthesis, particularly DNA synthesis. The subject compositions comprise an enzyme mixture for DNA synthesis comprising a first enzyme and a second enzyme, where the first enzyme comprises a DNA polymerization activity, and the second enzyme comprises a 3'-5' exonuclease activity and a reduced DNA polymerization activity. In addition to providing high fidelity for DNA synthesis, the compositions of the subject invention prevent side effects of a high polymerization activity, therefore, increase the efficiency of the amplification compared to a mixture in which both DNA polymerases possess wild-type polymerization activities.

DEFINITIONS

As used herein, "synthesis" refers to any in vitro method for making new strand of polynucleotide or elongating existing polynucleotide (i.e., DNA or RNA). Synthesis, according to the invention, include amplification, which increases the number of copies of a polynucleotide template sequence with the use of a polymerase. Polynucleotide synthesis (e.g., amplification) results in the incorporation of nucleotides into a polynucleotide (i.e., a primer), thereby forming a new polynucleotide molecule complementary to the polynucleotide template. The formed polynucleotide molecule and its template can be used as templates to synthesize additional polynucleotide molecules.

"DNA synthesis", according to the invention, includes, but are not limited to PCR, reverse transcription, the labelling of polynucleotide (i.e., for probes and oligonucleotide primers), polynucleotide sequencing.

As used herein, the term "template dependent manner" is intended to refer to a process that involves the template dependent extension of a primer molecule (e.g., DNA synthesis by DNA polymerase). The term "template dependent manner" refers to polynucleotide synthesis of RNA or DNA wherein the sequence of the newly synthesized strand of polynucleotide is dictated by the well-known rules of complementary base pairing (see, for example, Watson, J. D. et al., In: *Molecular Biology of the Gene*, 4th Ed., W. A. Benjamin, Inc., Menlo Park, Calif. (1987)).

As used herein, "polynucleotide polymerase" refers to an enzyme that catalyzes the polymerization of nucleotide. Generally, the enzyme will initiate synthesis at the 3'-end of the primer annealed to a polynucleotide template sequence, and will proceed toward the 5' end of the template strand. "DNA polymerase" catalyzes the polymerization of deoxynucleotides.

According to the invention, another class of DNA polymerase is "reverse transcriptases", also referred to as "RT", is a critical enzyme responsible for the synthesis of cDNA from viral RNA for all retroviruses, including HIV, HTLV-I, HTLV-II, FeLV, FIV, SIV, AMV, MMTV, and MoMuLV. For review, see e.g. Levin, 1997, Cell, 88:5-8; Brosius et al., 1995, Virus Genes 11:163-79. The term "reverse transcriptase (RT) activity" means the ability to synthesize cDNA from RNA template. Methods for measuring RT activity are well known in the art, for example, the Quan-T-RT assay system is commercially available from Amersham (Arlington Heights, Ill.) and is described in Bosworth, et al., Nature 1989, 341:167-168.

As used herein, a mutant DNA polymerase with "reduced polymerization activity" is a DNA polymerase mutant comprising a DNA polymerization activity which is lower than that of the wild-type enzyme, e.g., comprising less than 10% DNA (e.g., less than 8%, 6%, 4%, 2% or less than 1%) polymerization activity of that of the wild-type enzyme.

As used herein, "exonuclease" refers to an enzyme that cleaves bonds, preferably phosphodiester bonds, between nucleotides one at a time from the end of a DNA molecule. An exonuclease can be specific for the 5' or 3' end of a DNA molecule, and is referred to herein as a 5' to 3' exonuclease or a 3' to 5' exonuclease. A useful exonuclease according to the invention is a 3' to 5' exonuclease which degrades DNA by cleaving successive nucleotides from the 3' end of the polynucleotide. During the synthesis or amplification of a polynucleotide template, a DNA polymerase with 3' to 5' exonuclease activity (exo$^+$) has the capacity of removing mispaired base (proofreading activity), therefore is less error-prone than a DNA polymerase without 3' to 5' exonuclease activity (exo$^-$). The exonuclease activity can be defined by methods well known in the art. For example, one unit of exonuclease activity may refer to the amount of enzyme required to cleave 1 μg DNA target in an hour at 37° C. Wild type Tth DNA polymerase and Taq DNA polymerase are "exo$^-$" because they do not have 3' to 5' exonuclease activities, however, wild type Pfu DNA polymerase, *E. coli* DNA polymerase I, T7 DNA polymerase, Tma DNA polymerase, Tli DNA polymerase, KOD DNA polymerase, JDF DNA polymerse, and PGB-D DNA polymerase are "exo$^+$" because they all exhibit 3' to 5' exonuclease activity.

The term "fidelity" as used herein refers to the accuracy of DNA polymerization by template-dependent DNA polymerase. The fidelity of a DNA polymerase is measured by the error rate (the frequency of incorporating an inaccurate nucleotide, i.e., a nucleotide that is not incorporated at a template-dependent manner). The accuracy or fidelity of DNA polymerization is maintained by both the polymerase activity and the 3'-5' exonuclease activity of a DNA polymerase. The term "high fidelity" refers to an error rate of $5 \times 10^{-6}$ per base pair or lower. The fidelity or error rate of a DNA polymerase may be measured using assays known to the art (see for example, Lundburg et al., 1991 Gene, 108:1-6).

As used herein, an "amplified product" refers to the double strand polynucleotide population at the end of a PCR amplification reaction. The amplified product contains the original polynucleotide template and polynucleotide synthesized by DNA polymerase using the polynucleotide template during the PCR reaction.

As used herein, "polynucleotide template" or "target polynucleotide template" refers to a polynucleotide containing an amplified region. The "amplified region," as used herein, is a region of a polynucleotide that is to be either synthesized by reverse transcription or amplified by polymerase chain reaction (PCR). For example, an amplified region of a polynucleotide template resides between two sequences to which two PCR primers are complementary to.

As used herein, the term "primer" refers to a single stranded DNA or RNA molecule that can hybridize to a polynucleotide template and prime enzymatic synthesis of a second polynucleotide strand. A primer useful according to the invention is between 10 to 100 nucleotides in length, preferably 17-50 nucleotides in length and more preferably 17-45 nucleotides in length.

"Complementary" refers to the broad concept of sequence complementarity between regions of two polynucleotide strands or between two nucleotides through base-pairing. It is known that an adenine nucleotide is capable of forming specific hydrogen bonds ("base pairing") with a nucleotide which is thymine or uracil. Similarly, it is known that a cytosine nucleotide is capable of base pairing with a guanine nucleotide.

The term "wild-type" refers to a gene or gene product which has the characteristics of that gene or gene product when isolated from a naturally occurring source. In contrast, the term "modified" or "mutant" refers to a gene or gene product which displays altered characteristics when compared to the wild-type gene or gene product. For example, a mutant DNA polymerase in the present invention is a DNA polymerase which exhibit a reduced DNA polymerization activity.

As used herein, an "enzyme mixture" according to the invention, comprises a first enzyme comprising DNA polymerization activity and a second enzyme comprising a 3'-5' exonuclease activity and a reduced DNA polymerization activity. The ratio of the DNA polymerase activity and the exonuclease activity in the enzyme mixture is about (2.5-5 U of DNA polymerization activity)/(0.05-10 U of 3'-5' exonuclease activity).

Useful DNA Polymerases and Reverse Transcriptases

DNA polymerases and their properties are described in detail in, among other places, *DNA Replication* 2nd edition, Kornberg and Baker, W. H. Freeman, New York, N.Y. (1991).

Known conventional DNA polymerases include, for example, *Pyrococcus furiosus* (Pfu) DNA polymerase (Lundberg et al., 1991, *Gene*, 108:1, provided by Stratagene), *Pyrococcus woesei* (Pwo) DNA polymerase (Hinnisdaels et al., 1996, *Biotechniques*, 20:186-8, provided by Boehringer Mannheim), *Thermus thermophilus* (Tth) DNA polymerase (Myers and Gelfand 1991, *Biochemistry* 30:7661), *Bacillus stearothermophilus* DNA polymerase (Stenesh and McGowan, 1977, *Biochim Biophys Acta* 475:32), *Thermococcus litoralis* (Tli) DNA polymerase (also referred to as Vent DNA polymerase, Cariello et al., 1991, *Polynucleotides Res*, 19: 4193, provided by New England Biolabs), 9°Nm DNA polymerase (discontinued product from New England Biolabs), *Thermotoga maritima* (Tma) DNA polymerase (Diaz and Sabino, 1998 *Braz J. Med. Res*, 31:1239), *Thermus aquaticus* (Taq) DNA polymerase (Chien et al., 1976, J. Bacteriol, 127: 1550), *Pyrococcus kodakaraensis* KOD DNA polymerase (Takagi et al., 1997, *Appl. Environ. Microbiol.* 63:4504), JDF-3 DNA polymerase (from *thermococcus* sp. JDF-3, Patent application WO 0132887), *Pyrococcus* GB-D (PGB-D) DNA polymerase (also referred as Deep-Vent DNA polymerase, Juncosa-Ginesta et al., 1994, *Biotechniques*, 16:820, provided by New England Biolabs), U1Tma DNA.polymerase (from thermophile *Thermotoga maritima*; Diaz and Sabino, 1998 Braz J. Med. Res, 31:1239; provided by PE Applied Biosystems), Tgo DNA polymerase (from *thermococcus gorgonarius*, provided by Roche Molecular Biochemicals), *E. coli* DNA polymerase I (Lecomte and Doubleday, 1983, *Polynucleotides Res*. 11:7505), T7 DNA polymerase (Nordstrom et al., 1981, *J. Biol. Chem.* 256: 3112), and archaeal DP1/DP2 DNA polymerase II (Cann et al., 1998, Proc Natl Acad Sci USA 95:14250-5). The polymerization activity of any of the above enzymes can be defined by means well known in the art. One unit of DNA polymerization activity of conventional DNA polymerase, according to the subject invention, is defined as the amount of enzyme which catalyzes the incorporation of 10 nmoles of total deoxynucleotides (dNTPs) into polymeric form in 30 minutes at optimal temperature (e.g., 72° C. for Pfu DNA polymerase). Assays for DNA polymerase activity and 3'-5' exonuclease activity can be found in *DNA Replication* 2nd Ed., Kornberg and Baker, supra; *Enzymes*, Dixon and Webb, Academic Press, San Diego, Calif. (1979), as well as other publications available to the person of ordinary skill in the art.

When using the subject compositions in reaction mixtures that are exposed to elevated temperatures, e.g., during the PCR technique, use of thermostable DNA polymerases is preferred.

Reverse transcriptases useful according to the invention include, but are not limited to, reverse transcriptases from HIV, HTLV-1, HTLV-II, FeLV, FIV, SIV, AMV, MMTV, MoMuLV and other retroviruses (for reviews, see for example, Levin, 1997, Cell, 88:5-8; Verma, 1977, Biochim Biophys Acta. 473:1-38; Wu et al., 1975, CRC Crit Rev Biochem. 3:289-347).

Useful First Enzyme Comprising DNA Polymerization Activity

Enzymes comprising DNA polymerization activity according to the present invention include enzymes such as DNA polymerases and reverse transcriptases.

The first enzyme used in the subject composition can be any DNA polymerase, with or without a proof reading activity. Preferably, a wild type DNA polymerase is used. However, a mutant DNA polymerase can also be used so long as it provides sufficient DNA polymerization activity required for an amplification reaction.

In a preferred embodiment, the first enzyme comprising DNA polymerization activity is a wild type Pfu DNA polymerase. The enzyme mixture comprising a Pfu DNA polymerase as the first enzyme is also referred to as a Pfu blend herein after.

In preferred embodiments of the invention, a Pfu blend enzyme mixture is used for DNA synthesis reaction, e.g., PCR reaction.

In another preferred embodiment, the first enzyme comprising DNA polymerization activity is a wild type Taq DNA polymerase. The enzyme mixture comprising a Taq DNA polymerase as the first enzyme is also referred to as a Taq blend herein after.

In preferred embodiments of the invention, a Taq blend enzyme mixture is used for DNA synthesis reaction and for subsequent direct cloning, e.g., PCR reaction followed by TA cloning.

Useful Second Enzyme Comprising 3'-5' Exonuclease Activity

Enzyme comprising 3'-5' exonuclease activity (i.e., proofreading DNA polymerase) according to the invention include, but are not limited to, DNA polymerases, *E. coli* exonuclease I, *E. coli* exonuclease III, *E. coli* recBCD nuclease, mung bean nuclease, and the like (see for example, Kuo, 1994, Ann N Y Acad Sci., 726:223-34).

Any proofreading DNA polymerase could be mutagenized to reduce/eliminate DNA polymerase activity and used in the enzyme reaction of the present invention. Examples can be found in many DNA polymerase families including, but are not limited to such as follows:

Family B DNA Polymerases

Bacteriophage T4 DNA polymerase, φ29 DNA polymerase, T7 DNA polymerase; *E. coli* pol II DNA polymerase; human DNA polymerase δ, human DNA polymerase γ, archaeal DNA polymerase I (Table I).

Eubacterial Family A DNA Polymerases (with Proofreading Activity)

*E. coli* DNA pol I (Klenow fragment), *Thermotoga maritima* (U1Tma fragment)

Family D DNA Polymerases (Unrelated to Families A, B, C)

Archaeal DNA polymerase II (DP1/DP2) e.g., as described in Cann et al (1998) PNAS 95:14250-5.

TABLE I

Accession Information for Cloned Family B Polymerases

Vent *Thermococcus litoralis*
ACCESSION AAA72101
PID g348689
VERSION AAA72101.1 GI:348689
DBSOURCE locus THCVDPE accession M74198.1

TABLE I-continued

Accession Information for Cloned Family B Polymerases

THEST *THERMOCOCCUS* SP. (STRAIN TY)
ACCESSION O33845
PID g3913524
VERSION O33845 GI:3913524
DBSOURCE swissprot: locus DPOL_THEST, accession O33845
Pab *Pyrococcus abyssi*
ACCESSION P77916
PID g3913529
VERSION P77916 GI:3913529
DBSOURCE swissprot: locus DPOL_PYRAB, accession P77916
PYRHO *Pyrococcus horikoshii*
ACCESSION O59610
PID g3913526
VERSION O59610 GI:3913526
DBSOURCE swissprot: locus DPOL_PYRHO, accession O59610
PYRSE *PYROCOCCUS* SP. (STRAIN GE23)
ACCESSION P77932
PID g3913530
VERSION P77932 GI:3913530
DBSOURCE swissprot: locus DPOL_PYRSE, accession P77932
DeepVent *Pyrococcus* sp.
ACCESSION AAA67131
PID g436495
VERSION AAA67131.1 GI:436495
DBSOURCE locus PSU00707 accession U00707.1
Pfu *Pyrococcus furiosus*
ACCESSION P80061
PID g399403
VERSION P80061 GI:399403
DBSOURCE swissprot: locus DPOL_PYRFU, accession P80061
JDF-3 *Thermococcus* sp.
Unpublished
Baross gi|2097756|pat|US|5602011|12 Sequence 12 from patent US 5602011
9degN *THERMOCOCCUS* SP. (STRAIN 9ON-7).
ACCESSION Q56366
PID g3913540
VERSION Q56366 GI:3913540
DBSOURCE swissprot: locus DPOL_THES9, accession Q56366
KOD *Pyrococcus* sp.
ACCESSION BAA06142
PID g1620911
VERSION BAA06142.1 GI:1620911
DBSOURCE locus PYWKODPOL accession D29671.1
Tgo *Thermococcus gorgonarius*.
ACCESSION 4699806
PID g4699806
VERSION GI:4699806
DBSOURCE pdb: chain 65, release Feb. 23, 1999
THEFM *Thermococcus fumicolans*
ACCESSION P74918
PID g3913528
VERSION P74918 GI:3913528
DBSOURCE swissprot: locus DPOL_THEFM, accession P74918
METTH *Methanobacterium thermoautotrophicum*
ACCESSION O27276
PID g3913522
VERSION O27276 GI:3913522
DBSOURCE swissprot: locus DPOL_METTH, accession O27276
Metja *Methanococcus jannaschii*
ACCESSION Q58295
PID g3915679
VERSION Q58295 GI:3915679
DBSOURCE swissprot: locus DPOL_METJA, accession Q58295
POC *Pyrodictium occultum*
ACCESSION B56277
PID g1363344
VERSION B56277 GI:1363344
DBSOURCE pir: locus B56277
ApeI *Aeropyrum pernix*
ACCESSION BAA81109
PID g5105797
VERSION BAA81109.1 GI:5105797
DBSOURCE locus AP000063 accession AP000063.1
ARCFU *Archaeoglobus fulgidus*
ACCESSION O29753
PID g3122019
VERSION O29753 GI:3122019
DBSOURCE swissprot: locus DPOL_ARCFU, accession O29753
*Desulfurococcus* sp. *Tok*.
ACCESSION 6435708
PID g64357089
VERSION GT:6435708
DBSOURCE pdb. chain 65, release Jun. 2, 1999

Amino acid sequence of JDF-3 DNA polymerase (Sequence 2 of WO 01/32887):

(SEQ ID NO: 10)

```
Met Ile Leu Asp Val Asp Tyr Ile Thr Glu Asn Gly Lys Pro Val Ile
1               5                   10                  15

Arg Val Phe Lys Lys Glu Asn Gly Glu Phe Arg Ile Glu Tyr Asp Arg
            20                  25                  30

Glu Phe Glu Pro Tyr Phe Tyr Ala Leu Leu Arg Asp Asp Ser Ala Ile
            35                  40                  45

Glu Glu Ile Lys Lys Ile Thr Ala Glu Arg His Gly Arg Val Val Lys
        50                  55                  60

Val Lys Arg Ala Glu Lys Val Lys Lys Phe Leu Gly Arg Ser Val
65                  70                  75                  80

Glu Val Trp Val Leu Tyr Phe Thr His Pro Gln Asp Val Pro Ala Ile
                85                  90                  95

Arg Asp Lys Ile Arg Lys His Pro Ala Val Ile Asp Ile Tyr Glu Tyr
            100                 105                 110

Asp Ile Pro Phe Ala Lys Arg Tyr Leu Ile Asp Lys Gly Leu Ile Pro
            115                 120                 125

Met Glu Gly Glu Glu Glu Leu Lys Leu Met Ser Phe Asp Ile Glu Thr
        130                 135                 140

Leu Tyr His Glu Gly Glu Glu Phe Gly Thr Gly Pro Ile Leu Met Ile
145                 150                 155                 160
```

-continued

```
Ser Tyr Ala Asp Glu Ser Glu Ala Arg Val Ile Thr Trp Lys Lys Ile
                165                 170                 175

Asp Leu Pro Tyr Val Glu Val Val Ser Thr Glu Lys Glu Met Ile Lys
            180                 185                 190

Arg Phe Leu Arg Val Val Lys Glu Lys Asp Pro Asp Val Leu Ile Thr
        195                 200                 205

Tyr Asn Gly Asp Asn Phe Asp Phe Ala Tyr Leu Lys Lys Arg Cys Glu
    210                 215                 220

Lys Leu Gly Val Ser Phe Thr Leu Gly Arg Asp Gly Ser Glu Pro Lys
225                 230                 235                 240

Ile Gln Arg Met Gly Asp Arg Phe Ala Val Glu Val Lys Gly Arg Val
                245                 250                 255

His Phe Asp Leu Tyr Pro Val Ile Arg Arg Thr Ile Asn Leu Pro Thr
            260                 265                 270

Tyr Thr Leu Glu Ala Val Tyr Glu Ala Val Phe Gly Lys Pro Lys Glu
        275                 280                 285

Lys Val Tyr Ala Glu Glu Ile Ala Thr Ala Trp Glu Thr Gly Glu Gly
    290                 295                 300

Leu Glu Arg Val Ala Arg Tyr Ser Met Glu Asp Ala Arg Val Thr Tyr
305                 310                 315                 320

Glu Leu Gly Arg Glu Phe Phe Pro Met Glu Ala Gln Leu Ser Arg Leu
                325                 330                 335

Ile Gly Gln Gly Leu Trp Asp Val Ser Arg Ser Thr Gly Asn Leu
            340                 345                 350

Val Glu Trp Phe Leu Leu Arg Lys Ala Tyr Glu Arg Asn Glu Leu Ala
        355                 360                 365

Pro Asn Lys Pro Asp Glu Arg Glu Leu Ala Arg Arg Gly Gly Tyr
    370                 375                 380

Ala Gly Gly Tyr Val Lys Glu Pro Glu Arg Gly Leu Trp Asp Asn Ile
385                 390                 395                 400

Val Tyr Leu Asp Phe Arg Ser Leu Tyr Pro Ser Ile Ile Thr His
                405                 410                 415

Asn Val Ser Pro Asp Thr Leu Asn Arg Glu Gly Cys Arg Ser Tyr Asp
            420                 425                 430

Val Ala Pro Glu Val Gly His Lys Phe Cys Lys Asp Phe Pro Gly Phe
        435                 440                 445

Ile Pro Ser Leu Leu Gly Asn Leu Leu Glu Glu Arg Gln Lys Ile Lys
    450                 455                 460

Arg Lys Met Lys Ala Thr Leu Asp Pro Leu Glu Lys Asn Leu Leu Asp
465                 470                 475                 480

Tyr Arg Gln Arg Ala Ile Lys Ile Leu Ala Asn Ser Tyr Tyr Gly Tyr
                485                 490                 495

Tyr Gly Tyr Ala Arg Ala Arg Trp Tyr Cys Arg Glu Cys Ala Glu Ser
            500                 505                 510

Val Thr Ala Trp Gly Arg Glu Tyr Ile Glu Met Val Ile Arg Glu Leu
        515                 520                 525

Glu Glu Lys Phe Gly Phe Lys Val Leu Tyr Ala Asp Thr Asp Gly Leu
    530                 535                 540

His Ala Thr Ile Pro Gly Ala Asp Ala Glu Thr Val Lys Lys Lys Ala
545                 550                 555                 560

Met Glu Phe Leu Asn Tyr Ile Asn Pro Lys Leu Pro Gly Leu Leu Glu
                565                 570                 575

Leu Glu Tyr Glu Gly Phe Tyr Val Arg Gly Phe Phe Val Thr Lys Lys
            580                 585                 590
```

-continued

```
Lys Tyr Ala Val Ile Asp Glu Glu Gly Lys Ile Thr Thr Arg Gly Leu
            595                 600                 605
Glu Ile Val Arg Arg Asp Trp Ser Glu Ile Ala Lys Glu Thr Gln Ala
        610                 615                 620
Arg Val Leu Glu Ala Ile Leu Arg His Gly Asp Val Glu Glu Ala Val
625                 630                 635                 640
Arg Ile Val Arg Glu Val Thr Glu Lys Leu Ser Lys Tyr Glu Val Pro
                645                 650                 655
Pro Glu Lys Leu Val Ile His Glu Gln Ile Thr Arg Glu Leu Lys Asp
            660                 665                 670
Tyr Lys Ala Thr Gly Pro His Val Ala Ile Ala Lys Arg Leu Ala Ala
        675                 680                 685
Arg Gly Val Lys Ile Arg Pro Gly Thr Val Ile Ser Tyr Ile Val Leu
    690                 695                 700
Lys Gly Ser Gly Arg Ile Gly Asp Arg Ala Ile Pro Phe Asp Glu Phe
705                 710                 715                 720
Asp Pro Thr Lys His Lys Tyr Asp Ala Asp Tyr Tyr Ile Glu Asn Gln
                725                 730                 735
Val Leu Pro Ala Val Glu Arg Ile Leu Arg Ala Phe Gly Tyr Arg Lys
            740                 745                 750
Glu Asp Leu Arg Tyr Gln Lys Thr Arg Gln Val Gly Leu Gly Ala Trp
        755                 760                 765
Leu Lys Pro Lys Gly Lys Lys Lys
    770                 775
```

Nucleotide sequence of JDF-3 DNA polymerase (Sequence 1 of WO 01/32887)

```
                                                    (SEQ ID NO: 11)
atgatccttg acgttgatta catcaccgag aatggaaagc ccgtcatcag ggtcttcaag    60
aaggagaacg gcgagttcag gattgaatac gaccgcgagt tcgagcccta cttctacgcg   120
ctcctcaggg acgactctgc catcgaagaa atcaaaaaga taaccgcgga gaggcacggc   180
agggtcgtta aggttaagcg cgcggagaag gtgaagaaaa agttcctcgg caggtctgtg   240
gaggtctggg tcctctactt cacgcacccg caggacgttc cggcaatccg cgacaaaata   300
aggaagcacc ccgcggtcat cgacatctac gagtacgaca tacccttcgc caagcgctac   360
ctcatagaca agggcctaat cccgatggaa ggtgaggaag agcttaaact catgtccttc   420
gacatcgaga cgctctacca cgagggagaa gagtttggaa ccgggccgat tctgatgata   480
agctacgccg atgaaagcga ggcgcgcgtg ataacctgga gaagatcga ccttccttac   540
gttgaggttg tctccaccga gaaggagatg attaagcgct tcttgagggt cgttaaggag   600
aaggacccgg acgtgctgat aacatacaac ggcgacaact tcgacttcgc ctacctgaaa   660
aagcgctgtg agaagcttgg cgtgagcttt accctcggga gggacgggag agagccgaag   720
atacagcgca tggggacag gtttgcggtc gaggtgaagg gcagggtaca cttcgacctt   780
tatccagtca taaggcgcac cataaacctc ccgacctaca cccttgaggc tgtatacgag   840
gcggttttcg gcaagcccaa ggagaaggtc tacgccgagg atatagccac cgcctgggag   900
accggcgagg ggcttgagag ggtcgcgcgc tactcgatgg aggacgcgag ggttacctac   960
gagcttggca gggagttctt cccgatggag gcccagcttt ccaggctcat cggccaaggc  1020
ctctgggacg tttcccgctc cagcaccggc aacctcgtcg agtggttcct cctaaggaag  1080
gaatacgaga ggaacgaact cgctcccaac aagcccgacg agagggagct ggcgaggaga  1140
```

```
aggggggct  acgccggtgg  ctacgtcaag  gagccggagc  ggggactgtg  ggacaatatc  1200
gtgtatctag  actttcgtag  tctctaccct  tcaatcatcc  tcacccacaa  cgtctcgcca  1260
gatacgctca  accgcgaggg  gtgtaggagc  tacgacgttg  cccccgaggt  cggtcacaag  1320
ttctgcaagg  acttccccgg  cttcattccg  agcctgctcg  gaaacctgct  ggaggaaagg  1380
cagaagataa  agaggaagat  gaaggcaact  ctcgacccgc  tggagaagaa  tctcctcgat  1440
tacaggcaac  gcgccatcaa  gattctcgcc  aacagctact  acggctacta  cggctatgcc  1500
agggcaagat  ggtactgcag  ggagtgcgcc  gagagcgtta  cggcatgggg  aagggagtac  1560
atcgaaatgg  tcatcagaga  gcttgaggaa  aagttcggtt  ttaaagtcct  ctatgcagac  1620
acagacggtc  tccatgccac  cattcctgga  gcggacgctg  aaacagtcaa  gaaaaaggca  1680
atggagttct  taaactatat  caatcccaaa  ctgcccggcc  ttctcgaact  cgaatacgag  1740
ggcttctacg  tcagggctt   cttcgtcacg  aagaaaaagt  acgcggtcat  cgacgaggag  1800
ggcaagataa  ccacgcgcgg  gcttgagata  gtcaggcgcg  actggagcga  gatagcgaag  1860
gagacgcagg  cgagggtttt  ggaggcgata  ctcaggcacg  gtgacgttga  agaggccgtc  1920
agaattgtca  gggaagtcac  cgaaaagctg  agcaagtacg  aggttccgcc  ggagaagctg  1980
gttatccacg  agcagataac  gcgcgagctc  aaggactaca  aggccaccgg  cccgcacgta  2040
gccatagcga  agcgtttggc  cgccagaggt  gttaaaatcc  ggcccggaac  tgtgataagc  2100
tacatcgttc  tgaagggctc  cggaaggata  ggcgacaggg  cgattccctt  cgacgagttc  2160
gacccgacga  agcacaagta  cgatgcggac  tactacatcg  agaaccaggt  tctgccggca  2220
gttgagagaa  tcctcagggc  cttcggctac  cgcaaggaag  acctgcgcta  ccagaagacg  2280
aggcaggtcg  ggcttggcgc  gtggctgaag  ccgaagggga  agaagaagtg  a           2331
```

Enzymes possessing 3'-5' exonuclease activity for use in the present compositions and methods may be isolated from natural sources or produced through recombinant DNA techniques. Preferably, the enzyme comprising 3'-5' exonuclease activity is a DNA polymerase.

A DNA polymerase comprising 3'-5' exonuclease activity (referred as exo$^+$) is capable of proofreading the incorporated nucleotides produced by its own polymerization activity. Among other applications, exo$^+$ DNA polymerases are particularly suited for cloning of PCR products, characterization of polynucleotide sequences. Useful exo$^+$ DNA polymerases include, but are not limited to, Pwo DNA polymerase; Vent DNA polymerases; Deep Vent DNA polymerase; 9°Nm DNA polymerase; UlTma DNA polymerase; Tli DNA polymerase; Pfu DNA polymerase; JDF-3 DNA polymerase; Tgo DNA polymerase; KOD DNA polymerase; and PGB-D DNA polymerase.

In preferred embodiments of the subject invention, an exo$^+$ DNA polymerase with reduced DNA polymerization activity is used as the second enzyme.

Preparing Exo$^+$ DNA Polymerase with Reduced DNA Polymerization Activity

The cloned wild-type Exo$^+$ DNA polymerase may be modified to generate forms exhibiting reduced polymerization activity by a number of methods. These include the methods described below and other methods known in the art. Any exo$^+$ DNA polymerase can be used to prepare for the exo$^+$ DNA polymerase with reduced DNA polymerization activity in the invention.

A. Genetic Modifications—Mutagenesis

The preferred method of preparing a DNA polymerase with reduced polymerization activity is by genetic modification (e.g., by modifying the DNA sequence of a wild-type DNA polymerase). Within the sequence of an exo$^+$ DNA polymerase, the preferred sequence for genetic modification is the DNA sequence encoding the polymerization domain. Polymerization and exonuclease domains (i.e., their crystal structures) of many DNA polymerases are known in the art (for examples, see Rodriguez et al., 2000, J. Mol. Biol. 299: 447-62; Zhao et al., 1999, Structure Fold Des. 7:1189-99; Baker et al., 1998, Proc Natl Acad Sci USA. 95:3507-12; Kiefer et al., 1997, Structure 5:95-108; Kim et al., 1995, Nature, 376:612-6; Kong et al., 1993, J Biol Chem. 268:1965-75).

General structure features of DNA polymerization domain is known in the art. For example, Blanco et al. (1991, Gene, 100:27-38) discloses that significant amino acid (aa) sequence similarity has been found in the C-terminal portion of 27 DNA-dependent DNA polymerases belonging to the two main superfamilies: (i) *Escherichia coli* DNA polymerase I (PolI)-like prokaryotic DNA polymerases, and (ii) DNA polymerase alpha-like prokaryotic and eukaryotic (viral and cellular) DNA polymerases. The six most conserved C-terminal regions, spanning approximately 340 amino acids, are located in the same linear arrangement and contain highly conserved motifs and critical residues involved in the polymerization function.

According to the three-dimensional model of PolIk (Klenow fragment), these six conserved regions are located in the proposed polymerization domain, forming the metal and dNTP binding sites and the cleft for holding the DNA template. Site-directed mutagenesis studies support these structural predictions.

The 3'-5' exonuclease active site of E. coli DNA polymerase I is predicted to be conserved for both prokaryotic and eukaryotic DNA polymerases based on amino acid sequence homology (Bernad et al., 1989, Cell, 59:219-28). Three amino acid regions containing the critical residues in the E. coli DNA polymerase I involved in metal binding, single-stranded DNA binding, and catalysis of the exonuclease reaction are located in the amino-terminal half and in the same linear arrangement in several prokaryotic and eukaryotic DNA polymerases. Site-directed mutagenesis at the predicted exonuclease active site of the phi 29 DNA polymerase, a model enzyme for prokaryotic and eukaryotic alpha-like DNA polymerases, specifically inactivated the 3'-5' exonuclease activity of the enzyme. These results reflect a high evolutionary conservation of this catalytic domain.

With the great availability of sequences from DNA polymerases, it has become possible to delineate a few highly conserved regions for various polymerase types (for review, see for example, Johnson, 1993, Annu Rev Biochem. 62:685-713). Delarue et al. reported an approach for unifying the structure of DNA polymerase (1990, Protein Eng., 3:461-7). The speculative hypothesis should provide a useful model to direct genetic modifications for preparing DNA polymerase with reduced polymerization activity.

Preferably, the genetic modification for preparing exo$^+$ DNA polymerase with reduced polymerization activity does not significantly reduces its 3'-5' exonuclease activity (i.e., the proof reading activity).

Known DNA polymerase mutants that selectively reduce DNA polymerization activity can be found in the art, for example, in Blanco et al., 1995 Methods of Enzymology 262:283-294 ((Bacteriophage φ29); Truniger et al., 1996, EMBO J. 15:3430-3441 (Bacteriophage φ29); Abdus Sattar et al., 1996, Biochemistry 35:16621-9 (Bacteriophage T4); Tuske et al., 2000, J. Biological Chemistry 275:23759-68 (Klenow fragment); Bohlke et al., 2000, Nucleic Acid Research 28:3910-3917 (Thermococcus aggregans); Pisani et al., 1998, Biochemistry 37:15005-15012 (Sulfolobus solfataricus); Komori et al., 2000, Protein Eng 13:41-7 (Pyrococcus furiosus); Shen et al., 2001 J. Biological Chemistry 276:27376-83 (Pyrococcus horikoshi Family D).

Site-directed mutagenesis of bacteriophage φ29 DNA polymerase leads to the identification of mutations in the polymerase domain which reduce DNA polymerase activity, while having minimal effects on 3'-5' exonuclease activity (Blanco, L. and Salas, M. 1995, Methods of Enzymology 262:283-294). In one embodiment of the invention, one or more corresponding amino acids in Pfu DNA polymerases are mutated (e.g., by substitutions: D405E, Y410F, T542P, D543G, K593T, Y595S). It is understood that other amino acid side substitutions at these same sites would also selectively reduce DNA polymerase activity.

The φ29 DNA polymerase mutagenesis studies targeted amino acid residues within highly conserved Family B motifs (DXXSLYP [SEQ ID NO. 1], KXXXNSXYG [SEQ ID NO. 2], TXXGR [SEQ ID NO. 3], YXDTDS [SEQ ID NO. 4], and KXY [SEQ ID NO. 5]), although other regions of the protein presumably can be mutagenized to selectively decrease DNA polymerase activity. One such region is the partitioning domain, characterized by the YXGG [SEQ ID NO. 6] motif (Truniger et al., 1996, EMBO J. 15:3430-3441). This region is located within an accessible loop connecting the 3'-5' exonuclease and polymerase domains. The partitioning domain plays a critical role in coordinating the balance between synthesis and degradation of the DNA chain. Mutations within this region disrupt the equilibrium between polymerization and proofreading, and produce phenotypes favoring either polymerization (reduced proofreading) or proofreading (reduced polymerization).

Non-conservative (S,N) substitutions at $Y_{387}$ (equivalent to $Y_{385}$ in Pfu) in the partitioning domain of the archaeal Thermococcus aggregans DNA polymerase lead to a significant reduction in DNA polymerase activity and enhanced exonuclease activity, which results in improved enzyme fidelity (used alone in PCR) (Bohlke, K. et al (2000) NAR 28:3910-3917). In contrast, conservative substitutions at $Y_{387}$ (F, W, H) lead to wild-type-like fidelity and enhanced PCR performance, which may be related to improved polymerization. A G389A mutation (equivalent to Pfu G387) in Thermococcus aggregans DNA polymerase lead to reduced DNA polymerase activity (10% wt), increased exonuclease activity (236% wt), and loss of product synthesis in PCR (Bohlke, K. et al (2000) NAR 28:3910-3917). Analogous mutations have been investigated in bacteriophage φ29 DNA polymerase (Truniger, V., et al (1996) EMBO J. 15:3430-3441) and in the archaeal Solfolobus solfataricus (Sso) DNA polymerase (Pisani, F. M., DeFelice, M., and Rossi, M. (1998) Biochemistry 37:15005-15012), where a G→A mutation either decreases (pol/exo=0.6 for Sso) or increases (pol/exo=91 for φ29) DNA polymerase activity relative to exonuclease activity.

In one embodiment of the invention, Pfu DNA polymerase was mutated within the partitioning domain at amino acids 384-389 (SYTGGF [SEQ ID NO. 7]) to obtain a Pfu DNA polymerase with reduced polymerization activity. It is understood that other amino acid side substitutions within the partitioning domain, e.g., at positions Y385, G387, G388, could also selectively reduce DNA polymerase activity while having minimal effects on exonuclease activity.

In another embodiment, two or mutations are combined (e.g., by introducing additional site-directed mutations into a mutant Pfu DNA polymerase) to effectively eliminate DNA polymerase activity, while retaining high levels of proofreading activity.

U.S. Pat. Nos. 5,691,142, 5,614,402 and 5,541,311 disclose methods of deriving 5'-3' nucleases from thermostable DNA polymerases for the detection of target polynucleotide molecules (hereby incorporated by reference). These methods can be applied to the subject invention for preparing DNA polymerase comprising 3'-5' exonuclease activity with a reduced polymerization activity. Other techniques for genetic modification are well known in the art (see for example, Ausubel et. al. Short Protocols in Molecular Biology (1995) $3^{rd}$ Ed. John Wiley & Sons, Inc.).

Modification to the primary structure of a wild type enzyme by deletion, addition, or alteration of the amino acids incorporated into the sequence during translation can be made without destroying the high temperature DNA polymerase activity of the protein. Such substitutions or other alterations result in proteins useful in the methods of the present invention. The availability of DNA encoding these sequences provides the opportunity to modify the codon sequence to generate mutant enzymes having reduced polymerization activity. A few methods for altering DNA sequences are provided below, any other method known in the art may also be used.

There are a number of site-directed mutagenesis methods known in the art which allow one to mutate a particular site or region in a straightforward manner, based on the sequences of the polymerization domain of a DNA polymerase. There are a number of kits available commercially for the performance of site-directed mutagenesis, including both conventional and PCR-based methods. Examples include the EXSITE™ PCR- Based Site-directed Mutagenesis Kit available from Stratagene (Catalog No. 200502) and the QUIKCHANGE™ Site-directed mutagenesis Kit from Stratagene (Catalog No. 200518), and the CHAMELEON® double-stranded Site-directed mutagenesis kit, also from Stratagene (Catalog No. 200509).

Older methods of site-directed mutagenesis known in the art relied upon sub-cloning of the sequence to be mutated into a vector, such as an M13 bacteriophage vector, that allows the isolation of single-stranded DNA template. In these methods one anneals a mutagenic primer (i.e., a primer capable of annealing to the site to be mutated but bearing one or mismatched nucleotides at the site to be mutated) to the single-stranded template and then polymerizes the complement of the template starting from the 3' end of the mutagenic primer. The resulting duplexes are then transformed into host bacteria and plaques are screened for the desired mutation.

More recently, site-directed mutagenesis has employed PCR methodologies, which have the advantage of not requiring a single-stranded template. In addition, methods have been developed that do not require sub-cloning. Several issues must be considered when PCR-based site-directed mutagenesis is performed. First, in these methods it is desirable to reduce the number of PCR cycles to prevent expansion of undesired mutations introduced by the polymerase. Second, a selection must be employed in order to reduce the number of non-mutated parental molecules persisting in the reaction. Third, an extended-length PCR method is preferred in order to allow the use of a single PCR primer set. And fourth, because of the non-template-dependent terminal extension activity of some thermostable polymerases it is often necessary to incorporate an end-polishing step into the procedure prior to blunt-end ligation of the PCR-generated mutant product.

The protocol described below accommodates these considerations through the following steps. First, the template concentration used is approximately 1000-fold higher than that used in conventional PCR reactions, allowing a reduction in the number of cycles from 25-30 down to 5-10 without dramatically reducing product yield. Second, the restriction endonuclease DpnI (recognition target sequence: 5-Gm6ATC-3, where the A residue is methylated) is used to select against parental DNA, since most common strains of $E. coli$ Dam methylate their DNA at the sequence 5-GATC-3. Third, Taq Extender is used in the PCR mix in order to increase the proportion of long (i.e., full plasmid length) PCR products. Finally, Pfu DNA polymerase is used to polish the ends of the PCR product prior to intramolecular ligation using T4 DNA ligase.

A non-limiting example for the method is described in detail as follows:

Plasmid template DNA (approximately 0.5 pmole) is added to a PCR cocktail containing: 1× mutagenesis buffer (20 mM Tris HCl, pH 7.5; 8 mM $MgCl_2$; 40 µg/ml BSA); 12-20 pmole of each primer (one of skill in the art may design a mutagenic primer as necessary, giving consideration to those factors such as base composition, primer length and intended buffer salt concentrations that affect the annealing characteristics of oligonucleotide primers; one primer must contain the desired mutation, and one (the same or the other) must contain a 5' phosphate to facilitate later ligation), 250 µM each dNTP, 2.5 U Taq DNA polymerase, and 2.5 U of Taq Extender (Available from Stratagene; See Nielson et al. (1994) Strategies 7: 27, and U.S. Pat. No. 5,556,772). Primers can be prepared using the triester method of Matteucci et al., 1981, J. Am. Chem. Soc. 103:3185-3191, incorporated herein by reference. Alternatively automated synthesis may be preferred, for example, on a Biosearch 8700 DNA Synthesizer using cyanoethyl phosphoramidite chemistry.

The PCR cycling is performed as follows: 1 cycle of 4 min at 94° C., 2 min at 50° C. and 2 min at 72° C.; followed by 5-10 cycles of 1 min at 94° C., 2 min at 54° C. and 1 min at 72° C. The parental template DNA and the linear, PCR-generated DNA incorporating the mutagenic primer are treated with DpnI (10 U) and Pfu DNA polymerase (2.5 U). This results in the DpnI digestion of the in vivo methylated parental template and hybrid DNA and the removal, by Pfu DNA polymerase, of the non-template-directed Taq DNA polymerase-extended base(s) on the linear PCR product. The reaction is incubated at 37° C. for 30 min and then transferred to 72° C. for an additional 30 min. Mutagenesis buffer (115 ul of 1×) containing 0.5 mM ATP is added to the DpnI-digested, Pfu DNA polymerase-polished PCR products. The solution is mixed and 10 ul are removed to a new microfuge tube and T4 DNA ligase (2-4 U) is added. The ligation is incubated for greater than 60 min at 37° C. Finally, the treated solution is transformed into competent $E. coli$ according to standard methods.

Methods of random mutagenesis which will result in a panel of mutants bearing one or more randomly-situated mutations exist in the art. Such a panel of mutants may then be screened for those exhibiting reduced polymerization relative to the wild-type polymerase (e.g., by measuring the incorporation of 10 nmoles of dNTPs into polyperic form in 30 minutes at the optimal temperature for a given DNA polymerase). An example of a method for random mutagenesis is the so-called "error-prone PCR method". As the name implies, the method amplifies a given sequence under conditions in which the DNA polymerase does not support high fidelity incorporation. The conditions encouraging error-prone incorporation for different DNA polymerases vary, however one skilled in the art may determine such conditions for a given enzyme. A key variable for many DNA polymerases in the fidelity of amplification is, for example, the type and concentration of divalent metal ion in the buffer. The use of manganese ion and/or variation of the magnesium or manganese ion concentration may therefore be applied to influence the error rate of the polymerase.

In a preferred embodiment, the second enzyme with reduced polymerization activity is derived form Pfu DNA polymerase.

The DNA coding sequence of a wild-type Pfu DNA polymerase can be found in the art, for example, from Genbank (accession No. U84155). A detailed description of the structure and function of Pfu DNA polymerase can be found, among other places in U.S. Pat. Nos. 5,948,663; 5,866,395; 5,545,552; 5,556,772, all of which thereby incorporated by references. As disclosed in U.S. Pat. No. 5,948,663, the wild type Pfu DNA polymerase comprises the following amino acid sequence:

```
                                                  (SEQ ID NO. 12)
Met Ile Leu Asp Val Asp Tyr Ile Thr Glu Glu Gly Lys Pro Val Ile
1               5                   10                  15

Arg Leu Phe Lys Lys Glu Asn Gly Lys Phe Lys Ile Glu His Asp Arg
            20                  25                  30
```

-continued

```
Thr Phe Arg Pro Tyr Ile Tyr Ala Leu Leu Arg Asp Asp Ser Lys Ile
        35                  40                  45

Glu Glu Val Lys Lys Ile Thr Gly Arg His Gly Lys Ile Val Arg
 50                  55                  60

Ile Val Asp Val Glu Lys Val Glu Lys Phe Leu Gly Lys Pro Ile
65                  70                  75                  80

Thr Val Trp Lys Leu Tyr Leu Glu His Pro Gln Asp Val Pro Thr Ile
                85                  90                  95

Arg Glu Lys Val Arg Glu His Pro Ala Val Val Asp Ile Phe Glu Tyr
                100                 105                 110

Asp Ile Pro Phe Ala Lys Arg Tyr Leu Ile Asp Lys Gly Leu Ile Pro
                115                 120                 125

Met Glu Gly Glu Glu Leu Lys Ile Leu Ala Phe Asp Ile Glu Thr
130                 135                 140

Leu Tyr His Glu Gly Glu Phe Gly Lys Gly Pro Ile Ile Met Ile
145                 150                 155                 160

Ser Tyr Ala Asp Glu Asn Glu Ala Lys Val Ile Thr Trp Lys Asn Ile
                165                 170                 175

Asp Leu Pro Tyr Val Glu Val Val Ser Ser Glu Arg Glu Met Ile Lys
                180                 185                 190

Arg Phe Leu Arg Ile Ile Arg Glu Lys Asp Pro Asp Ile Ile Val Thr
                195                 200                 205

Tyr Asn Gly Asp Ser Phe Asp Phe Pro Tyr Leu Ala Lys Arg Ala Glu
                210                 215                 220

Lys Leu Gly Ile Lys Leu Thr Ile Gly Arg Asp Gly Ser Glu Pro Lys
225                 230                 235                 240

Met Gln Arg Ile Gly Asp Met Thr Ala Val Glu Val Lys Gly Arg Ile
                245                 250                 255

His Phe Asp Leu Tyr His Val Ile Thr Arg Thr Ile Asn Leu Pro Thr
                260                 265                 270

Tyr Thr Leu Glu Ala Val Tyr Glu Ala Ile Phe Gly Lys Pro Lys Glu
                275                 280                 285

Lys Val Tyr Ala Asp Glu Ile Ala Lys Ala Trp Glu Ser Gly Glu Asn
                290                 295                 300

Leu Glu Arg Val Ala Lys Tyr Ser Met Glu Asp Ala Lys Ala Thr Tyr
305                 310                 315                 320

Glu Leu Gly Lys Glu Phe Leu Pro Met Glu Ile Gln Leu Ser Arg Leu
                325                 330                 335

Val Gly Gln Pro Leu Trp Asp Val Ser Arg Ser Ser Thr Gly Asn Leu
                340                 345                 350

Val Glu Trp Phe Leu Leu Arg Lys Ala Tyr Glu Arg Asn Glu Val Ala
                355                 360                 365

Pro Asn Lys Pro Ser Glu Glu Glu Tyr Gln Arg Arg Leu Arg Glu Ser
                370                 375                 380

Tyr Thr Gly Gly Phe Val Lys Glu Pro Glu Lys Gly Leu Trp Glu Asn
385                 390                 395                 400

Ile Val Tyr Leu Asp Phe Arg Ala Leu Tyr Pro Ser Ile Ile Ile Thr
                405                 410                 415

His Asn Val Ser Pro Asp Thr Leu Asn Leu Glu Gly Cys Lys Asn Tyr
                420                 425                 430

Asp Ile Ala Pro Gln Val Gly His Lys Phe Cys Lys Asp Ile Pro Gly
                435                 440                 445

Phe Ile Pro Ser Leu Leu Gly His Leu Leu Glu Glu Arg Gln Lys Ile
450                 455                 460
```

```
Lys Thr Lys Met Lys Glu Thr Gln Asp Pro Ile Glu Lys Ile Leu Leu
465                 470                 475                 480

Asp Tyr Arg Gln Lys Ala Ile Lys Leu Leu Ala Asn Ser Phe Tyr Gly
                485                 490                 495

Tyr Tyr Gly Tyr Ala Lys Ala Arg Trp Tyr Cys Lys Glu Cys Ala Glu
            500                 505                 510

Ser Val Thr Ala Trp Gly Arg Lys Tyr Ile Glu Leu Val Trp Lys Glu
        515                 520                 525

Leu Glu Glu Lys Phe Gly Phe Lys Val Leu Tyr Ile Asp Thr Asp Gly
    530                 535                 540

Leu Tyr Ala Thr Ile Pro Gly Gly Glu Ser Glu Glu Ile Lys Lys Lys
545                 550                 555                 560

Ala Leu Glu Phe Val Lys Tyr Ile Asn Ser Lys Leu Pro Gly Leu Leu
                565                 570                 575

Glu Leu Glu Tyr Glu Gly Phe Tyr Lys Arg Gly Phe Phe Val Thr Lys
            580                 585                 590

Lys Arg Tyr Ala Val Ile Asp Glu Glu Gly Lys Val Ile Thr Arg Gly
            595                 600                 605

Leu Glu Ile Val Arg Arg Asp Trp Ser Glu Ile Ala Lys Glu Thr Gln
    610                 615                 620

Ala Arg Val Leu Glu Thr Ile Leu Lys His Gly Asp Val Glu Glu Ala
625                 630                 635                 640

Val Arg Ile Val Lys Glu Val Ile Gln Lys Leu Ala Asn Tyr Glu Ile
                645                 650                 655

Pro Pro Glu Lys Leu Ala Ile Tyr Glu Gln Ile Thr Arg Pro Leu His
            660                 665                 670

Glu Tyr Lys Ala Ile Gly Pro His Val Ala Val Ala Lys Lys Leu Ala
        675                 680                 685

Ala Lys Gly Val Lys Ile Lys Pro Gly Met Val Ile Gly Tyr Ile Val
    690                 695                 700

Leu Arg Gly Asp Gly Pro Ile Ser Asn Arg Ala Ile Leu Ala Glu Glu
705                 710                 715                 720

Tyr Asp Pro Lys Lys His Lys Tyr Asp Ala Glu Tyr Tyr Ile Glu Asn
                725                 730                 735

Gln Val Leu Pro Ala Val Leu Arg Ile Leu Glu Gly Phe Gly Tyr Arg
            740                 745                 750

Lys Glu Asp Leu Arg Tyr Gln Lys Thr Arg Gln Val Gly Leu Thr Ser
        755                 760                 765

Trp Leu Asn Ile Lys Lys Ser
770                 775
```

A not-limiting detailed procedure for preparing Pfu DNA polymerase with reduced polymerization activity is provided in Example 1.

A person of average skill in the art having the benefit of this disclosure will recognize that polymerases with reduced polymerization activity derived from other exo+ DNA polymerases including Vent DNA polymerase, JDF-3 DNA polymerase, Tgo DNA polymerase and the like may be suitably used in the subject compositions.

The first or the second enzyme of the subject composition may comprise DNA polymerases that have not yet been isolated. Assays for both DNA polymerization activity and 3'-5' exonuclease activity can be found in the subject description and in *DNA Replication* 2nd Ed., Kornberg and Baker, supra; *Enzymes*, Dixon and Webb, Supra, as well as other publications available to the person of ordinary skill in the art.

In preferred embodiments of the invention, mutant Pfu DNA polymerase comprises one or more mutations at amino acid positions selected from the group consisting of: D405, Y410, T542, D543, K593, Y595, Y385, G387, and G388.

More preferably, the mutant Pfu DNA polymerase comprises one or more mutations selected from the group consisting of: D405E, Y410F, T542P, D543G, K593T, Y595S, Y385Q, Y385S, Y385N, Y385L, Y385H, G387S, G387P, and G388P.

B. Methods of Evaluating Mutants for Reduced Polymerization

Random or site-directed mutants generated as known in the art or as described herein and expressed in bacteria may be screened for reduced polymerization by several different assays. Embodiments for the expression of mutant and wild type enzymes is described herein below in section C. In one method, exo+ DNA polymerase proteins expressed in lytic lambda phage plaques generated by infection of host bacteria with expression vectors based on, for example, Lambda ZapII®, are transferred to a membrane support. The immobilized proteins are then assayed for polymerase activity on the membrane by immersing the membranes in a buffer containing a DNA template and the unconventional nucleotides to be monitored for incorporation.

Mutant polymerase libraries may be screened using a variation of the technique used by Sagner et al (Sagner, G., Ruger, R., and Kessler, C. (1991) Gene 97:119-123). For this approach, lambda phage clones are plated at a density of 10-20 plaques per square centimeter. Proteins present in the plaques are transferred to filters and moistened with polymerase screening buffer (50 mM Tris (pH 8.0), 7 mM $MgCl_2$, 3 mM β-ME). The filters are kept between layers of plastic wrap and glass while the host cell proteins are heat-inactivated by incubation at 65° C. for 30 minutes. The heat-treated filters are then transferred to fresh plastic wrap and approximately 35l of polymerase assay cocktail are added for every square centimeter of filter. The assay cocktail consists of 1× cloned Pfu (cPfu) magnesium free buffer (1× buffer is 20 mM Tris-HCl (pH 8.8), 10 mM KCl, 10 mM $(NH4)_2SO_4$, 100 μg/ml bovine serum albumin (BSA), and 0.1% Triton X-100; Pfu Magnesium-free buffer may be obtained from Stratagene (Catalog No. 200534)), 125 ng/ml activated calf thymus or salmon sperm DNA, 1.29 μCi/ml α-$^{33}$P ddNTP. The filters are placed between plastic wrap and a glass plate and then incubated at 65° C. for one hour, and then at 70° C. for one hour and fifteen minutes. Filters are then washed three times in 2×SSC for five minutes per wash before rinsing twice in 100% ethanol and vacuum drying. Filters are then exposed to X-ray film (approximately 16 hours), and plaques that incorporate label are identified by aligning the filters with the original plate bearing the phage clones. Plaques identified in this way are re-plated at more dilute concentrations and assayed under similar conditions to allow the isolation of purified plaques.

In assays such as the one described above, the signal generated by the label is a direct measure of the polymerization activity of the polymerase. A plaque comprising a mutant DNA polymerase with reduced DNA polymerization activity compared to that of the wild-type enzyme can be selected.

Incorporation of nucleotides may also be measured in extension reactions by adding, for example, 1 μl of appropriately diluted bacterial extract (i.e., heat-treated and clarified extract of bacterial cells expressing a cloned polymerase or mutated cloned polymerase) to 10 μl of each nucleotide cocktail, followed by incubation at the optimal temperature for 30 minutes (e.g., 73° C. for Pfu DNA polymerase), for example, as described in Hogrefe et al., 2001, Methods in Enzymology, 343:91-116. Extension reactions are quenched on ice, and then 5 μl aliquots are spotted immediately onto DE81 ion-exchange filters (2.3 cm; Whatman #3658323). Unincorporated label is removed by 6 washes with 2×SCC (0.3M NaCl, 30 mM sodium citrate, pH 7.0), followed by a brief wash with 100% ethanol. Incorporated radioactivity is then measured by scintillation counting. Reactions that lack enzyme are also set up along with sample incubations to determine "total cpms" (omit filter wash steps) and "minimum cpms" (wash filters as above). Cpms bound is proportional to the amount of polymerase activity present per volume of bacterial extract.

A Non-limiting method for determining polymerization activity of a DNA polymerase is provided as follows. Percent radioactivity incorporation which indicates the polymerization activity of a DNA polymerase can be determined as:

$$\frac{(\text{corrected cpms for mutants}) \times (\text{ng wt Pfu})}{(\text{corrected cpms for wt Pfu}) \times (\text{ng mutant Pfu})}.$$

To more precisely quantify % activity, one should covert cpms incorporated into units of DNA polymerase activity. One unit of polymerase activity is defined as the amount of enzyme that catalyzes the incorporation of 10 nmoles of total dNTP into polymeric form (e.g., binds to DE-81 paper) in 30 minutes at optimal temperature. Units of DNA polymerase activity can be calculated using the following equation:

$$\frac{(\text{corrected sample cpms})}{\text{total cpms}} \times \frac{(8 \text{ nmoles dNTPs})}{\text{reaction}} \frac{(1 \text{ unit})}{(10 \text{ nmoles dNTPs incorporated})}$$

Polymerase specific activity (U/mg) can be extrapolated from the slope of the linear portion of units versus enzyme amount plots. Protein concentrations can be determined relative to a BSA standard (Pierce) in a colorimetric assay (e.g. Pierce's Coomassie Plus Protein Assay). Alternatively, when protein amounts are limiting (or for preparations of limited purity), relative protein concentrations can be verified by SDS-PAGE analysis. Several aliquots of each DNA polymerase preparation, ranging from 1-20 ng of total protein, are subject to SDS-PAGE electrophoresis and the intensity of silver- and/or Sypro orange (Molecular Probes)-stained bands are compared to standards. Finally, % activity can be determined as:

$$\frac{\text{specific polymerase activity (U/mg) of mutant}}{\text{specific polymerase activity (U/mg) of wt Pfu}}$$

It is preferred that the polymerases with reduced polymerization activity of the present invention maintain their proofreading activities (i.e., 3'-5' exonuclease activities). The mutant DNA polymerases with reduced DNA polymerization activities, therefore, are also assayed for 3'-5-exonuclease activities.

Suitable exonuclease activity assays include one described in Hogrefe et al (supra, and as described in Example 3). Another ne assay employs double-stranded λ DNA, which has been uniformly labeled with $^3$H S-adenosyl methionine (NEN #NET-155) and Sss I methylase (NEB), and then restriction digested with Pal I (Kong et al., 1993, J. Biol. Chem. 268:1965). Using double-stranded labeled DNA templates, one can determine specificity by measuring whether cpms increase or decrease (3'-5' exonuclease) with the addition of dNTPs (10-100 μM). A typical exonuclease reaction cocktail consists of 1× reaction buffer and 20 μg/ml $^3$H-labeled digested double-stranded λ DNA (~$10^6$ cpms/ml), prepared as described (Kong et al., supra). Exonuclease activity can be measured in the appropriate PCR buffer or in a universal assay buffer such as 70 mM Tris HCl (pH 8.8), 2 mM $MgCl_2$, 0.1% Triton-X, and 100 μg/ml BSA.

Percent exonuclease activity can be determined as: (corrected cpms for mutants)/(corrected cpms for wt Pfu). To more precisely quantify % activity, cpms released can be converted into units of exonuclease activity. One unit of exonuclease activity is defined as the amount of enzyme that catalyzes the acid-solubilization of 10 nmoles of total dNMPs in 30 minutes at a defined temperature. To determine units, background (average "minimum cpms" value) is first subtracted from the average sample cpms. Nmoles dNMPs released is calculated using the following equation:

$$\frac{\text{(corrected sample cpms)}}{\text{total cpms}} \times \frac{\text{(920 ng DNA)}}{\text{reaction}} \frac{\text{(1 nmole dNMP)}}{\text{(330 ng dNMP)}}$$

Units of exonuclease activity (in 30 minutes) can then be determined as:

$$\frac{\text{(nmoles dNMPs released per hr)}}{2} \times \frac{\text{(1 unit)}}{\text{(10 nmoles dNMPs released)}}$$

Exonuclease specific activity (U/mg) can be extrapolated from the slope of the linear portion of units versus enzyme amount plots. Finally, % activity can be determined as:

$$\frac{\text{specific exonuclease activity (U/mg) of mutant}}{\text{specific exonuclease activity (U/mg) of wt Pfu}}$$

In addition to the substrate described above, exonuclease activity can be also be quantified using [$^3$H]-*E. coli* genomic DNA (NEN #NET561; 5.8 μCi/μg), a commercially-available substrate. A typical exonuclease reaction cocktail consists of 0.4 μg/ml $^3$H-labeled *E. coli* genomic DNA in 1× reaction buffer. Assays are performed as described above.

Genes for desired mutant DNA polymerases generated by mutagenesis may be sequenced to identify the sites and number of mutations. For those mutants comprising more than one mutation, the effect of a given mutation may be evaluated by introduction of the identified mutation to the wild-type gene by site-directed mutagenesis in isolation from the other mutations borne by the particular mutant. Screening assays of the single mutant thus produced will then allow the determination of the effect of that mutation alone.

In one embodiment, the Pfu mutant is G387P, which reduces the error rate of wild type Pfu DNA polymerase by 3-fold in Pfu blend and the error rate of Taq by 5- to 8-fold in Taq blend when added at 0.6-3.6 μg/50 μl reaction. Pfu G387P exhibited 0.4% DNA polymerase activity and 57% exonuclease activity (i.e., relative to wild type Pfu) in a preliminary screen of partially purified (~50% purity) His-tagged proteins, eluted from nickel columns (Table 1). After column chromatography (~95% purity), the Pfu G387P mutant was found to be devoid of detectable DNA polymerase activity (<0.01% activity relative to wild type Pfu) (Table 2).

C. Expression of Wild-Type or Mutant Enzymes According to the Invention

Methods known in the art may be applied to express and isolate the mutated forms of DNA polymerase (i.e., the second enzyme) according to the invention. The methods described here can be also applied for the expression of wild-type enzymes useful (e.g., the first enzyme) in the invention. Many bacterial expression vectors contain sequence elements or combinations of sequence elements allowing high level inducible expression of the protein encoded by a foreign sequence. For example, as mentioned above, bacteria expressing an integrated inducible form of the T7 RNA polymerase gene may be transformed with an expression vector bearing a mutated DNA polymerase gene linked to the T7 promoter. Induction of the T7 RNA polymerase by addition of an appropriate inducer, for example, isopropyl-β-D-thiogalactopyranoside (IPTG) for a lac-inducible promoter, induces the high level expression of the mutated gene from the T7 promoter.

Appropriate host strains of bacteria may be selected from those available in the art by one of skill in the art. As a non-limiting example, *E. coli* strain BL-21 is commonly used for expression of exogenous proteins since it is protease deficient relative to other strains of *E. coli*. BL-21 strains bearing an inducible T7 RNA polymerase gene include WJ56 and ER2566 (Gardner & Jack, 1999, supra). For situations in which codon usage for the particular polymerase gene differs from that normally seen in *E. coli* genes, there are strains of BL-21 that are modified to carry tRNA genes encoding tRNAs with rarer anticodons (for example, argU, ileY, leuW, and proL tRNA genes), allowing high efficiency expression of cloned protein genes, for example, cloned archaeal enzyme genes (several BL21-CODON PLUS™ cell strains carrying rare-codon tRNAs are available from Stratagene, for example).

There are many methods known to those of skill in the art that are suitable for the purification of a modified DNA polymerase of the invention. For example, the method of Lawyer et al. (1993, *PCR Meth. & App.* 2: 275) is well suited for the isolation of DNA polymerases expressed in *E. coli*, as it was designed originally for the isolation of Taq polymerase. Alternatively, the method of Kong et al. (1993, J. Biol. Chem. 268: 1965, incorporated herein by reference) may be used, which employs a heat denaturation step to destroy host proteins, and two column purification steps (over DEAE-Sepharose and heparin-Sepharose columns) to isolate highly active and approximately 80% pure DNA polymerase. Further, DNA polymerase mutants may be isolated by an ammonium sulfate fractionation, followed by Q Sepharose and DNA cellulose columns, or by adsorption of contaminants on a HiTrap Q column, followed by gradient elution from a HiTrap heparin column.

In one embodiment, the Pfu mutants are expressed and purified as described in U.S. Pat. No. 5,489,523, thereby incorporated by reference in its entirety.

D. Other Methods for Reducing Polymerization Activity

In order to prevent the side effects of having a high DNA polymerization activity in an amplification reaction, the polymerization activity of the composition of the invention may also be reduced by physical and/or chemical modification and/or inhibition.

The polymerization activity of the subject composition may be reduced by chemical and/or physical means. Conditions which preferentially inhibit the polymerization activity of a DNA polymerase is known in the art (for reviews, see Johnson, 1993, supra; Wright, 1996, Acta Biochim Pol. 43:115-24; Elion, 1982, Am J Med., 73:7-13). The level of polymerization activity need only be reduced to that level of activity which does not interfere with amplification reactions (e.g., does not significantly affect the exo$^+$ activity of the composition or the efficiency yield of the amplification reaction).

Concentrations of Mg$^{2+}$ greater than 5 mM inhibit the polymerization activity of the Pfu DNA polymerase. The effect of a given concentration of Mg$^{2+}$ for a given DNA polymerase may be determined by quantitation of the efficiency and specificity of polymerization.

The inhibitory effect of other ions, polyamines, denaturants, such as urea, formamide, dimethylsulfoxide, glycerol and non-ionic detergents (Triton X-100 and Tween-20), polynucleotide binding chemicals such as, actinomycin D, ethidium bromide and psoralens, may be tested by their addition to the standard reaction buffers for polynucleotide amplification (e.g., PCR). Those compounds having a preferential inhibitory effect on the polymerization activity but not significantly affecting the 3'-5' exonuclease activity of a DNA polymerase are then used to create reaction conditions under which 3'-5' nuclease activity is retained while polymerization activity is reduced.

Physical means may be used to preferentially inhibit the polymerization activity of a polymerase. For example, the polymerization activity of thermostable polymerases is destroyed by exposure of the polymerase to extreme heat (typically 96° C. to 100° C.) for extended periods of time (greater than or equal to 20 minutes). While there are minor differences with respect to the specific heat tolerance for each of the enzymes, these are readily determined. The polymerase mixture of the invention or the exo+ DNA polymerase used as the second enzyme with reduced polymerization activity can be treated with heat for various periods of time and the effect of the heat treatment upon the polymerization and 3'-5' nuclease activities is determined. Conditions reducing DNA polymerase activity but not significantly affecting the 3'-5' exonuclease activity may be used to pretreat the polymerase mixture or the exo+ DNA polymerase used as second enzyme with reduced polymerization activity in the present invention.

Enzyme Mixture

The subject enzyme mixture composition comprises a first enzyme comprising DNA polymerization activity and a second enzyme comprising 3'-5' exonuclease activity with reduced DNA polymerase activity.

In one embodiment, the first enzyme is a DNA polymerase with 3'-5' exonuclease activity. The fidelity of the first enzyme for DNA amplification is increased by the use of a second enzyme which also possesses 3'-5' exonuclease activity. A preferred DNA polymerase with 3'-5' exonuclease activity as the first enzyme is a wild type Pfu DNA polymerase.

In another embodiment, the first enzyme is a DNA polymerase without 3'-5' exonuclease activity. The fidelity of an amplification reaction is provided by the second enzyme of the subject invention, which possesses 3'-5' exonuclease activity. A preferred DNA polymerase without 3'-5' exonuclease activity as the first enzyme is a Taq DNA polymerase.

In yet another embodiment, the first enzyme may is a reverse transcriptase with DNA polymerization activity. The fidelity of the reverse transcriptase in cDNA synthesis is increased by the use of a second enzyme which possesses 3'-5' exonuclease activity.

A. Selection of the First and the Second Enzyme Pair

In the subject method for DNA synthesis, any enzyme comprising DNA polymerization activity may be mixed with a second enzyme comprising 3'-5' exonuclease activity and reduced polymerization activity.

When both first and second enzymes in the mixture comprise 3'-5' exonuclease activity, it may be desirable to combine two enzymes with different proofreading activities. By "different proofreading activity", it means that two 3'-5' exonucleases exhibits different proofreading preference for a nucleotide. For example, one 3'-5' exonuclease may proofread a G-T mispair more efficiently than an A-A mispair, another exonuclease having a different proofreading preference may proofread an A-A mispair more efficiently than a G-T mispair. By using a second enzyme with a different proofreading preference from the first enzyme of the subject composition, one can enhance proofreading of the first enzyme by providing proofreading to mispairs which the first enzyme is not capable of recognizing and excising efficiently.

Another factor to consider when selecting the first and the second enzymes of the subject invention is the compatibility of reaction conditions (e.g., pH, buffer composition, temperature requirement, etc.) required by each enzyme.

In a preferred embodiment, the subject composition comprises a wild-type Pfu DNA polymerase as the first enzyme and a mutant Pfu DNA polymerase with reduced DNA polymerization activity as the second enzyme. Preferably, the mixture comprises a ratio of 2.5-5 U Pfu DNA polymerase plus an amount of a polymerase reduced mutant corresponding to <0.1 U DNA polymerase activity and 0.05 U to 10 U of 3'-5' exonuclease activity (or the amount of exonuclease activity containing within 2.5-500 U wild type Pfu). More preferably, the mixture comprises a ratio of 2.5-5 U Pfu DNA polymerase plus an amount of a polymerase reduced mutant corresponding to <0.01 U DNA polymerase activity and 0.5 U to 1.7 U of 3'-5' exonuclease activity (or the amount of exonuclease activity contained within 30-90 U wild type Pfu)

In another preferred embodiment, the subject composition comprises a wild-type Taq DNA polymerase as the first enzyme and a mutant Pfu DNA polymerase with reduced DNA polymerization activity as the second enzyme. Preferably, the enzyme mixture comprises a ration of 2.5 U Taq DNA polymerase plus an amount of a polymerase deficient mutant corresponding to <0.00125 U DNA polymerase activity and 0.05 U to 10 U of 3'-5' exonuclease activity (or the amount of exonuclease activity contained within 2.5-500 U wild type Pfu). More preferably, the enzyme mixture comprises a ratio of 2.5 U Taq DNA polymerase plus an amount of a polymerase deficient mutant corresponding to <0.00125 U DNA polymerase activity and 0.5 U to ≥3 U of 3'-5' exonuclease activity (or the amount of exonuclease activity contained within 30 to ≥160 U wild type Pfu).

Preferably the mutant Pfu DNA polymerase with reduced DNA polymerization activity comprises one or more mutations at amino acid positions selected from the group consisting of: D405, Y410, T542, D543, K593, Y595, Y385, G387, and G388.

More preferably, the mutant Pfu DNA polymerase comprises one or more mutations selected from the group consisting of: D405E, Y410F, T542P, D543G, K593T, Y595S, Y385Q, Y385S, Y385N, Y385L, Y385H, G387S, G387P, and G388P.

B. the Ratio of Polymerization to Exonuclease Activity in the Enzyme Mixture

In a variety of DNA synthesis and amplification procedures, the compositions of the present invention provide superior synthesis results (e.g., higher fidelity and efficiency), as compared with the synthesis results obtained with a single DNA polymerase or with a mixture comprising two wild type DNA polymerases. When using the subject composition, the ratio of total polymerization activity and total exonuclease activity in the enzyme mixture may be critical for optimal efficiency and fidelity of DNA synthesis.

In the enzyme mixture of the subject invention, when DNA polymerases are used as the first and second enzymes, both enzymes may contribute to the polymerization and/or 3'-5' exonuclease activity. When an enzyme other than a conventional DNA polymerase is used as the first enzyme (e.g., a reverse transcriptase), both enzymes may contribute to DNA polymerization activity, but only the second enzyme contribute to the 3'-5' exonuclease activity. When an enzyme other than a DNA polymerase is used as the second enzyme (e.g., *E. coli* exonuclease I), both enzymes may contribute to the 3'-5' exonuclease activity, but only the first enzyme contribute to the polymerization activity of the enzyme mixture.

The ratio of the first and the second enzyme in the subject composition may be varied with respect to one another. The ratio of the DNA polymerization activity to 3'-5' exonuclease activity present in the subject composition employed in a given synthesis procedure may be readily optimized by performing a series of simple experiments in which the ratio of the DNA polymerization activity to the exonuclease activity in the reaction mixture are systematically varied with respect to one another and the synthesis results compared.

3'-5' exonuclease activity has been shown to degrade unannealed primers. The degraded primers would not be available in subsequent rounds of DNA amplification and would therefore effect the efficiency of the PCR reaction. In applications requiring very high product yield, it may therefore be desirable to have a low concentration of the exonuclease activity relative to the DNA polymerization activity to decrease this effect and to increase the product yield. However, when fidelity is more important than yield, it may be desirable to have a high concentration of the exonuclease activity relative to the DNA polymerization activity to increase the accuracy of the synthesis or amplification so long as the level of polymerization activity does not significantly inhibit the efficiency of the amplification.

In a preferred embodiment, the ratio of the DNA polymerase activity and the exonuclease activity in the enzyme mixture is about (2.5-5 U of DNA polymerization activity)/(0.05-10 U of 3'-5' exonuclease activity).

Applications of the Subject Invention

In one aspect, the invention provides a method for DNA synthesis using the compositions of the subject invention. The subject compositions may be used in various methods of polynucleotide synthesis in essentially the same manner as the DNA polymerase or other synthetic enzyme present in the subject composition. Typically, synthesis of a polynucleotide requires a synthesis primer, a synthesis template, polynucleotide precursors for incorporation into the newly synthesized polynucleotide, (e.g. dATP, dCTP, dGTP, dTTP), and the like. Detailed methods for carrying out polynucleotide synthesis are well known to the person of ordinary skill in the art and can be found, for example, in *Molecular Cloning second edition*, Sambrook et al., Cold Spring Harbor Laboratory Press, Cold Spring Harbor, N.Y. (1989).

A. Application in Amplification Reactions

"Polymerase chain reaction" or "PCR" refers to an in vitro method for amplifying a specific polynucleotide template sequence. The technique of PCR is described in numerous publications, including, PCR: A Practical Approach, M. J. McPherson, et al., IRL Press (1991), PCR Protocols: A Guide to Methods and Applications, by Innis, et al., Academic Press (1990), and PCR Technology: Principals and Applications for DNA Amplification, H. A. Erlich, Stockton Press (1989). PCR is also described in many U.S. Patents, including U.S. Pat. Nos. 4,683,195; 4,683,202; 4,800,159; 4,965,188; 4,889,818; 5,075,216; 5,079,352; 5,104,792; 5,023,171; 5,091,310; and 5,066,584, each of which is herein incorporated by reference.

For ease of understanding the advantages provided by the present invention, a summary of PCR is provided. The PCR reaction involves a repetitive series of temperature cycles and is typically performed in a volume of 50-100 µl. The reaction mix comprises dNTPs (each of the four deoxynucleotides dATP, dCTP, dGTP, and dTTP), primers, buffers, DNA polymerase, and polynucleotide template. PCR requires two primers that hybridize with the double-stranded target polynucleotide sequence to be amplified. In PCR, this double-stranded target sequence is denatured and one primer is annealed to each strand of the denatured target. The primers anneal to the target polynucleotide at sites removed from one another and in orientations such that the extension product of one primer, when separated from its complement, can hybridize to the other primer. Once a given primer hybridizes to the target sequence, the primer is extended by the action of a DNA polymerase. The extension product is then denatured from the target sequence, and the process is repeated.

In successive cycles of this process, the extension products produced in earlier cycles serve as templates for DNA synthesis. Beginning in the second cycle, the product of amplification begins to accumulate at a logarithmic rate. The amplification product is a discrete double-stranded DNA molecule comprising: a first strand which contains the sequence of the first primer, eventually followed by the sequence complementary to the second primer, and a second strand which is complementary to the first strand.

Due to the enormous amplification possible with the PCR process, small levels of DNA carryover from samples with high DNA levels, positive control templates or from previous amplifications can result in PCR product, even in the absence of purposefully added template DNA. If possible, all reaction mixes are set up in an area separate from PCR product analysis and sample preparation. The use of dedicated or disposable vessels, solutions, and pipettes (preferably positive displacement pipettes) for RNA/DNA preparation, reaction mixing, and sample analysis will minimize cross contamination. See also Higuchi and Kwok, 1989, Nature, 339:237-238 and Kwok, and Orrego, in: Innis et al. eds., 1990, *PCR Protocols: A Guide to Methods and Applications*, Academic Press, Inc., San Diego, Calif., which are incorporated herein by reference.

1. Thermostable Enzymes

For PCR amplifications, the enzymes used in the invention are preferably thermostable. As used herein, "thermostable" refers to an enzyme which is stable to heat, is heat resistant, and functions at high temperatures, e.g., 50 to 90° C. The thermostable enzyme according to the present invention must satisfy a single criterion to be effective for the amplification reaction, i.e., the enzyme must not become irreversibly denatured (inactivated) when subjected to the elevated temperatures for the time necessary to effect denaturation of double-stranded polynucleotides. By "irreversible denaturation" as used in this connection, is meant a process bringing a permanent and complete loss of enzymatic activity. The heating conditions necessary for denaturation will depend, e.g., on the buffer salt concentration and the length and nucleotide composition of the polynucleotides being denatured, but typically range from 85° C., for shorter polynucleotides, to 105° C. for a time depending mainly on the temperature and the polynucleotide length, typically from 0.25 minutes for shorter polynucleotides, to 4.0 minutes for longer pieces of DNA. Higher temperatures may be tolerated as the buffer salt concentration and/or GC composition of the polynucleotide is increased. Preferably, the enzyme will not become irreversibly denatured at 90 to 100° C. An enzyme that does not become irreversibly denatured, according to the invention, retains at least 10%, or at least 25%, or at least 50% or more function or activity during the amplification reaction.

2. PCR Reaction Mixture

In addition to the subject enzyme mixture, one of average skill in the art may also employ other PCR parameters to increase the fidelity of synthesis/amplification reaction. It has been reported PCR fidelity may be affected by factors such as changes in dNTP concentration, units of enzyme used per reaction, and the ratio of $Mg^{2+}$ to dNTPs present in the reaction (Mattila et al., 1991, supra).

$Mg^{2+}$ concentration affects the annealing of the oligonucleotide primers to the template DNA by stabilizing the primer-template interaction, it also stabilizes the replication complex of polymerase with template-primer. It can therefore also increases non-specific annealing and produced undesirable PCR products (gives multiple bands in gel). When non-specific amplification occurs, $Mg^{2+}$ may need to be lowered or EDTA can be added to chelate $Mg^{2+}$ to increase the accuracy and specificity of the amplification.

Other divalent cations such as $Mn^{2+}$, or $Co^{2+}$ can also affect DNA polymerization. Suitable cations for each DNA polymerase are known in the art (e.g., in *DNA Replication* $2^{nd}$ *edition*, supra). Divalent cation is supplied in the form of a salt such $MgCl_2$, $Mg(OAc)_2$, $MgSO_4$, $MnCl_2$, $Mn(OAc)_2$, or $MnSO_4$. Usable cation concentrations in a Tris-HCl buffer are for $MnCl_2$ from 0.5 to 7 mM, preferably, between 0.5 and 2 mM, and for $MgCl_2$ from 0.5 to 10 mM. Usable cation concentrations in a Bicine/KOAc buffer are from 1 to 20 mM for $Mn(OAc)_2$, preferably between 2 and 5 mM.

Monovalent cation required by DNA polymerase may be supplied by the potassium, sodium, ammonium, or lithium salts of either chloride or acetate. For KCl, the concentration is between 1 and 200 mM, preferably the concentration is between 40 and 100 mM, although the optimum concentration may vary depending on the polymerase used in the reaction.

Deoxyribonucleotide triphosphates (dNTPs) are added as solutions of the salts of dATP, dCTP, dGTP, dUTP, and dTTP, such as disodium or lithium salts. In the present methods, a final concentration in the range of 1 µM to 2 mM each is suitable, and 100-600 µM is preferable, although the optimal concentration of the nucleotides may vary in the reverse transcription reaction depending on the total dNTP and divalent metal ion concentration, and on the buffer, salts, particular primers, and template. For longer products, i.e., greater than 1500 bp, 500 µM each dNTP may be preferred when using a Tris-HCl buffer.

dNTPs chelate divalent cations, therefore amount of divalent cations used may need to be changed according to the dNTP concentration in the reaction. Excessive amount of dNTPs (e.g., larger than 1.5 mM) can increase the error rate and possibly inhibits DNA polymerases. Lowering the dNTP (e.g., to 10-50 µM) may therefore reduce error rate. PCR reaction for amplifying larger size template may need more dNTPs.

One suitable buffering agent is Tris-HCl, preferably pH 8.3, although the pH may be in the range 8.0-8.8. The Tris-HCl concentration is from 5-250 mM, although 10-100 mM is most preferred. A preferred buffering agent is Bicine-KOH, preferably pH 8.3, although pH may be in the range 7.8-8.7. Bicine acts both as a pH buffer and as a metal buffer.

PCR is a very powerful tool for DNA amplification therefore very little template DNA is needed. However, in some embodiments, to reduce the likelihood of error, a higher DNA concentration may be used, though too many templates may increase the amount of contaminants and reduce efficiency.

Usually, up to 3 µM of primers may be used, but high primer to template ratio can results in non-specific amplification and primer-dimer formation. Therefore it is usually necessary to check primer sequences to avoid primer-dimer formation.

3. Cycling Parameters

Denaturation time may be increased if template GC content is high. Higher annealing temperature may be needed for primers with high GC content or longer primers. Gradient PCR is a useful way of determining the annealing temperature. Extension time should be extended for larger PCR product amplifications. However, extension time may need to be reduced whenever possible to limit damage to enzyme.

The number of cycle can be increased if the number of template DNA is very low, and decreased if high amount of template DNA is used.

4. PCR Enhancing Factors and Additives

PCR enhancing factors may also be used to improve efficiency of the amplification. As used herein, a "PCR enhancing factor" or a "Polymerase Enhancing Factor" (PEF) refers to a complex or protein possessing polynucleotide polymerase enhancing activity (Hogrefe et al., 1997, Strategies 10:93-96; and U.S. Pat. No. 6,183,997, both of which are hereby incorporated by references). For Pfu DNA polymerase, PEF comprises either P45 in native form (as a complex of P50 and P45) or as a recombinant protein. In the native complex of Pfu P50 and P45, only P45 exhibits PCR enhancing activity. The P50 protein is similar in structure to a bacterial flavoprotein. The P45 protein is similar in structure to dCTP deaminase and dUTPase, but it functions only as a dUTPase converting dUTP to dUMP and pyrophosphate. PEF, according to the present invention, can also be selected from the group consisting of: an isolated or purified naturally occurring polymerase enhancing protein obtained from an archeabacteria source (e.g., *Pyrococcus furiosus*); a wholly or partially synthetic protein having the same amino acid sequence as Pfu P45, or analogs thereof possessing polymerase enhancing activity; polymerase-enhancing mixtures of one or more of said naturally occurring or wholly or partially synthetic proteins; polymerase-enhancing protein complexes of one or more of said naturally occurring or wholly or partially synthetic proteins; or polymerase-enhancing partially purified cell extracts containing one or more of said naturally occurring proteins (U.S. Pat. No. 6,183,997, supra). The PCR enhancing activity of PEF is defined by means well known in the art. The unit definition for PEF is based on the dUTPase activity of PEF (P45), which is determined by monitoring the production of pyrophosphate (PPi) from dUTP. For example, PEF is incubated with dUTP (10 mM dUTP in 1× cloned Pfu PCR buffer) during which time PEF hydrolyzes dUTP to dUMP and PPi. The amount of PPi formed is quantitated using a coupled enzymatic assay system that is commercially available from Sigma (#P7275). One unit of activity is functionally defined as 4.0 nmole of PPi formed per hour (at 85° C.).

Other PCR additives may also affect the accuracy and specificity of PCR reaction. EDTA less than 0.5 mM may be present in the amplification reaction mix. Detergents such as Tween-20™ and Nonidet™ P-40 are present in the enzyme dilution buffers. A final concentration of non-ionic detergent approximately 0.1% or less is appropriate, however, 0.01-0.05% is preferred and will not interfere with polymerase activity. Similarly, glycerol is often present in enzyme preparations and is generally diluted to a concentration of 1-20% in the reaction mix. Glycerol (5-10%), formamide (1-5%) or DMSO (2-10%) can be added in PCR for template DNA with high GC content or long length (e.g., >1 kb). These additives change the Tm (melting temperature) of primer-template hybridization reaction and the thermostability of polymerase enzyme. BSA (up to 0.8 µg/µl) can improve efficiency of PCR reaction. Betaine (0.5-2M) is also useful for PCR over high GC content and long fragments of DNA. Tetramethylammonium chloride (TMAC, >50 mM), Tetraethylammonium chloride (TEAC), and Trimethlamine N-oxide (TMANO) may also be used. Test PCR reactions may be performed to determine optimum concentration of each additive mentioned above.

Various specific PCR amplification applications are available in the art (for reviews, see for example, Erlich, 1999, *Rev Immunogenet.*, 1:127-34; Prediger 2001, *Methods Mol. Biol.*

160:49-63; Jurecic et al., 2000, *Curr. Opin. Microbiol.* 3:316-21; Triglia, 2000, *Methods Mol. Biol.* 130:79-83; MaClelland et al., 1994, *PCR Methods Appl.* 4:S66-81; Abramson and Myers, 1993, *Current Opinion in Biotechnology* 4:41-47; each of which is incorporated herein by references).

The subject invention can be used in PCR applications include, but are not limited to, i) hot-start PCR which reduces non-specific amplification; ii) touch-down PCR which starts at high annealing temperature, then decreases annealing temperature in steps to reduce non-specific PCR product; iii) nested PCR which synthesizes more reliable product using an outer set of primers and an inner set of primers; iv) inverse PCR for amplification of regions flanking a known sequence. In this method, DNA is digested, the desired fragment is circularized by ligation, then PCR using primer complementary to the known sequence extending outwards; v) AP-PCR (arbitrary primed)/RAPD (random amplified polymorphic DNA). These methods create genomic fingerprints from species with little-known target sequences by amplifying using arbitrary oligonucleotides; vi) RT-PCR which uses RNA-directed DNA polymerase (e.g., reverse transcriptase) to synthesize cDNAs which is then used for PCR. This method is extremely sensitive for detecting the expression of a specific sequence in a tissue or cells. It may also be use to quantify mRNA transcripts; vii) RACE (rapid amplification of cDNA ends). This is used where information about DNA/protein sequence is limited. The method amplifies 3' or 5' ends of cDNAs generating fragments of cDNA with only one specific primer each (plus one adaptor primer). Overlapping RACE products can then be combined to produce full length cDNA; viii) DD-PCR (differential display PCR) which is used to identify differentially expressed genes in different tissues. First step in DD-PCR involves RT-PCR, then amplification is performed using short, intentionally nonspecific primers; ix) Multiplex-PCR in which two or more unique targets of DNA sequences in the same specimen are amplified simultaneously. One DNA sequence can be use as control to verify the quality of PCR; x) Q/C-PCR (Quantitative comparative) which uses an internal control DNA sequence (but of different size) which compete with the target DNA (competitive PCR) for the same set of primers; xi) Recusive PCR which is used to synthesize genes. Oligonucleotides used in this method are complementary to stretches of a gene (>80 bases), alternately to the sense and to the antisense strands with ends overlapping (~20 bases); xii) Asymmetric PCR; xiii) In Situ PCR; xiv) Site-directed PCR Mutagenesis.

It should be understood that this invention is not limited to any particular amplification system. As other systems are developed, those systems may benefit by practice of this invention. A recent survey of amplification systems was published in.

B. Applications in Reverse Transcription

The term "reverse transcriptase" describes a class of polymerase characterized as RNA-dependent DNA polymerases. All known reverse transcriptases require a primer to synthesize a DNA transcript from an RNA template. Historically, reverse transcriptase has been used primarily to transcribe mRNA into cDNA which can then be cloned into a vector for further manipulation (e.g., PCR amplification by a DNA-dependent DNA polymerase).

Avian myoblastosis virus (AMV) reverse transcriptase was the first widely used RNA-dependent DNA polymerase (Verma, 1977, Biochem. Biophys. Acta 473:1). The enzyme has 5'-3' RNA-directed DNA polymerase activity, 5'-3' DNA-directed DNA polymerase activity, and RNase H activity. RNase H is a processive 5' and Y ribonuclease specific for the RNA strand of RNA-DNA hybrids (Perbal, 1984, *A Practical Guide to Molecular Cloning*, Wiley & Sons New York). Errors in transcription cannot be corrected by reverse transcriptase because known viral reverse transcriptases lack the 3'-5' exonuclease activity necessary for proofreading (Saunders and Saunders, 1987, *Microbial Genetics Applied to Biotechnology*, Croom Helm, London). The use of the second enzyme in the subject composition provides proofreading for the reverse transcription reaction. A detailed study of the activity of AMV reverse transcriptase and its associated RNase H activity has been presented by Berger et al., 1983, Biochemistry 22:2365-2372.

The reaction mixture for reverse transcription usually includes enzymes, aqueous buffers, salts, oligonucleotide primers, target polynucleotide, and nucleoside triphosphates. Depending upon the context, the mixture can be either a complete or incomplete reverse transcription reaction mixture. The reaction mixture can be modified according to the conditions required by the second enzyme of the subject composition. It is known that cDNAs can be obtained from mRNAs in vitro using a reverse transcriptase (RNA-dependent DNA polymerase). The full length cDNA strands produced in turn may be used as a template for subsequent amplification reaction (e.g., PCR) and the like.

Reverse transcription in combination with PCR (RT-PCT) is utilized to detect the presence of one or many specific RNA molecules which may be present in a sample. The method can be used to detect, for example, RNA from different organisms (such as viruses, bacteria, fungi, plants, and animals), or RNA indicative of an infection, a disease state, or predisposition to a disease. For example, mRNA specific to tumor cells can be detected. The method is also useful for detecting a class of microorganisms or a group of related disease conditions.

Reverse transcription can generally be performed at any temperature within the functional temperature range of the reverse transcriptase. Preferably, the temperature of incubation is any temperature at which the reverse transcriptase is functional and the primer remains hybridized to the RNA molecule. For non-thermostable reverse transcriptases, preferred temperatures are those temperatures that are at or around the optimum temperature for the reverse transcriptase. For most non-thermostable reverse transcriptases this temperature will be between about 25° C. and 45° C.

U.S. Pat. No. 5,994,079 discloses thermostable reverse transcriptases (herein incorporated by reference). $Mn^{2+}$ is preferred as the divalent cation and is typically included as a salt, for example, manganese chloride ($MnCl_2$), manganese acetate ($Mn(OAc)_2$), or manganese sulfate ($MnSO_4$). If $MnCl_2$ is included in a reaction containing 10 mM Tris buffer, for example, the $MnCl_2$ is generally present at a concentration of 0.5-7.0 mM; 0.8-1.4 mM is preferred when 200 µM of each dGTP, dATP, dUTP, and, dCTP are utilized; an 1.2 mM $MnCl_2$ is most preferred.

A thermostable reverse transcriptase may retain at least 5% of its maximum activity at any temperature above 50° C. or has an optimal temperature of at least 50° C. The highest temperature at which a thermostable reverse transcriptase is functional can be quite high. For this reason, preferred temperature ranges for reverse transcription when a thermostable reverse transcriptase is used are most conveniently described in terms of the calculated melting temperature of a hybrid between the RNA molecule of interest and the primer. Such a melting temperature is referred to herein as the RNA/primer melting temperature (R/P Tm). Preferred ranges include a temperature from 20° C. below the melting temperature of a hybrid between the RNA molecule of interest and the primer and 5° C. above the melting temperature of a hybrid between the RNA molecule of interest and the primer. In general, the closer the temperature is to the R/P Tm, the greater the degree of discrimination there will be between specific and non-specific hybrids of the RNA and primer. If the temperature is close to the R/P Tm, however, decreased stability of specific hybrids may cause priming to be less efficient.

R/P Tm can be determined either by calculation or by empirical measurement. For calculating R/P Tm, any established formula for calculating stability of polynucleotide hybrids can be used. A preferred formula for calculating R/P Tm is Tm=81.5+16.6(log M)$^+$0.41(% G$^+$C)−0.72(% formamide), which was derived from studies on the stability of perfectly-matched DNA:DNA hybrids. For RNA:DNA hybrids, incorporating formamide concentration in the formula does not hold because the relationship between formamide concentration and the depression of Tm is not linear. At 80% formamide, RNA:DNA hybrids are more stable than DNA:DNA hybrids, increasing the Tm by about 10 to 30° C. depending on the sequence (Hames & Higgins, Polynucleotide Hybridisation: A Practical Approach (IRL Press Limited, Oxford, England. 1985)). Carrying out the reaction in 80% formamide can therefore also be used to suppress formation of DNA:DNA duplexes, to preferentially select RNA:DNA hybrids, and to estimate the Tm for R/P. Because the empirically derived formulas for the estimation of RNA:DNA hybrid Tm may not be as accurate for short DNA primers, the hybridization temperature is preferably determined by assessing hybrid stability in 0.1-0.4 M monovalent cation at temperatures ranging from 40 to 60° C. R/P Tm can also be determined empirically (Lesnick and Freier, 1995, Biochemistry 34:10807-10815, McGraw et al., 1990, Biotechniques 8:674-678; and Rychlik et al., 1990, Polynucleotides Res. 18:6409-6412).

The fidelity of viral reverse transcriptases, such as AMV-RT and MoMuLV-RT, may be compared to thermoactive reverse transcriptases by a straightforward assay procedure described in U.S. Pat. No. 5,994,079 (supra). Plasmid BS$^+$ (Stratagene) can be used for such an assay. The plasmid encodes an α-complementing β-galactosidase activity and can be linearized with NdeI. T3 RNA polymerase is used to prepare a cRNA transcript of the α-donor region. After treatment of the cRNA with RNase-free DNase and isolation of the cRNA, the cRNA is used as a template for a reverse transcription/amplification reaction. A reverse transcription primer complementary to the 3' end of the cDNA containing an NdeI sequence at its 5' terminus, and an upstream PCR primer comprising a PstI sequence at the 5' termini provide a 752 bp PCR product. The PCR product and the pBS$^+$ vector are then digested with NdeI and PstI followed by ligation of the PCR product into the vector and transformation into a suitable host. The presence of white colonies indicates that a mutation had occurred during the RT or PCR amplification. The assay provides means for assigning a relative value to the fidelity of the reverse transcriptase activity of various enzymes. Specific mutations can be determined by sequence analysis.

Following reverse transcription of RNA, the RNA can be removed from the RNA/cDNA hybrid by heat denaturation or by a number of other known means such as alkali, heat, or enzyme treatment. Enzyme treatment may consist of, for example, treating the RNA/cDNA hybrid with RNase H. RNase H is specific for RNA strands within an RNA/DNA double-stranded molecule.

The subject composition is suitable for high fidelity transcribing and amplifying RNA from a number of sources. The RNA template may be contained within a polynucleotide preparation from an organism, for example, a viral or bacterial polynucleotide preparation. The preparation may contain cell debris and other components, purified total RNA, or purified mRNA. The RNA template may be a population of heterogeneous RNA molecules in a sample or a specific target RNA molecule.

RNA suitable for use in the present methods may be contained in a biological sample suspected of containing a specific target RNA. The biological sample may be a heterogeneous sample in which RNA is a small portion of the sample, as in for example, a blood sample or a biopsied tissue sample. Thus, the subject composition is useful for clinical detection and diagnosis. The RNA target may be indicative of a specific disease or infectious agent.

RNA may be prepared by any number of methods known in the art; the choice may depend on the source of the sample and availability. Methods for preparing RNA are described in Davis et al., 1986, *Basic Methods in Molecular Biology*, Elsevier, NY, Chapter 11; Ausubel et al., 1987, *Current Protocols in Molecular Biology*, Chapter 4, John Wiley and Sons, NY; Kawasaki and Wang, 1989, *PCR Technology*, ed. Erlich, Stockton Press NY; Kawasaki, 1990, *PCR Protocols: A Guide to Methods and Applications*, Innis et al. eds. Academic Press, San Diego; all of which are incorporated herein by references.

C. Detection of Amplified Product

Detection of amplified polynucleotide product can be accomplished by any of a variety of well known techniques. In a preferred embodiment, the amplified product is separated on the basis of molecular weight by gel electrophoresis, and the separated products are then visualized by the use of polynucleotide specific stains which allow one to observe the discrete species of resolved amplified product present in the gel. Although numerous polynucleotide specific stains exist and would be suitable to visualize the electrophoretically separated polynucleotides, ethidium bromide is preferred.

Alternative methods suitable to detect the amplified polynucleotide product include hybridization-based detection means that use a labeled polynucleotide probe capable of hybridizing to the amplified product. Exemplary of such detection means include the Southern blot analysis, ribonuclease protection analysis using in vitro labeled polyribonucleotide probes, and similar methods for detecting polynucleotides having specific nucleotide sequences. See, for example, Ausubel et al., *Current Protocols in Molecular Biology*, John Wiley & Sons, 1987.

Amplified products (e.g., by PCR or RT-PCR) using the subject composition of the invention can be used for subsequent analysis such as sequencing or cloning.

D. Application in Direct Cloning of PCR Amplified Product

While it is understood that the amplified product using subject composition can be cloned by any method known in the art. In one embodiment, the invention provides a composition which allows direct cloning of PCR amplified product.

The most common method for cloning PCR products involves incorporation of flanking restriction sites onto the ends of primer molecules. The PCR cycling is carried out and the amplified DNA is then purified, restricted with an appropriate endonuclease(s) and ligated to a compatible vector preparation.

A method for directly cloning PCR products eliminates the need for preparing primers having restriction recognition sequences and it would eliminate the need for a restriction step to prepare the PCR product for cloning. Additionally, such method would preferably allow cloning PCR products directly without an intervening purification step.

U.S. Pat. Nos. 5,827,657 and 5,487,993 (hereby incorporated by their entirety) discloses method for direct cloning of PCR products using a DNA polymerase which takes advantage of the single 3'-deoxy-adenosine monophosphate (dAMP) residues attached to the 3' termini of PCR generated nucleic acids. Vectors are prepared with recognition sequences that afford single 3'-terminal deoxy-thymidine monophosphate (dTMP) residues upon reaction with a suitable restriction enzyme. Thus, PCR generated copies of genes can be directly cloned into the vectors without need for preparing primers having suitable restriction sites therein.

Taq DNA polymerase exhibits terminal transferase activity that adds a single dATP to the 3' ends of PCR products in the absence of template. This activity is the basis for the TA cloning method in which PCR products amplified with Taq are directed ligated into vectors containing single 3' dT overhangs. Pfu DNA polymerase, on the other hand, lacks terminal transferase activity, and thus produces blunt-ended PCR products that are efficiently cloned into blunt-ended vectors.

In one embodiment, the subject invention comprises a Taq DNA polymerase as the first enzyme and a mutant Pfu DNA polymerase with reduced polymerization activity as the second enzyme. Taq DNA polymerase in the composition produces amplified DNA product with 3'-dAMP and allows direct cloning of the amplified product, while the mutant Pfu DNA polymerase provides fidelity for the amplification.

Kits

The invention herein also contemplates a kit format which comprises a package unit having one or more containers of the subject composition and in some embodiments including containers of various reagents used for polynucleotide synthesis, including synthesis in PCR. The kit may also contain one or more of the following items: polynucleotide precursors, primers, buffers, instructions, and controls. Kits may include containers of reagents mixed together in suitable proportions for performing the methods in accordance with the invention. Reagent containers preferably contain reagents in unit quantities that obviate measuring steps when performing the subject methods.

EXAMPLES

The following examples are offered for the purpose of illustrating, not limiting, the subject invention.

Example 1

Constructing Mutants of Pfu DNA Polymerase with Reduced DNA Polymerase Activity

We introduced mutations into Pfu DNA polymerase that were likely to reduce or eliminate DNA polymerase activity, while having minimal effects on proofreading activity. The mutations selected were identified from previous mutagenesis studies carried out using related Family B DNA polymerases. We made the same amino acid side chain substitutions in the polymerization domain at the following residues in Pfu (D405E, Y410F, T542P, D543G, K593T, Y595S) (Table 1).

Mutations were also introduced within the partitioning domain at amino acids 384-389 (SYTGGF) in Pfu DNA polymerase (Table 1).

The DNA template used for mutagenesis contained the Pfu pol gene, cloned into pBluescript (pF72 clone described in U.S. Pat. No. 5,489,523) and expressed with an N-terminal $His_6$ tag for affinity purification. A modified QuikChange (Stratagene) protocol was used to insert the $His_6$ tag at the 5' end of the Pfu pol gene, just after the initiator ATG. The insertion reaction was carried out in two steps. In the first step, a standard QuikChange reaction was carried out in the presence of Tth ligase (10 U/R×N) using only the $His_6$ forward primer. After 18 cycles, the reaction was DpnI-digested for one hour at 37° C. and then purified with the StrataPrep® Plasmid Miniprep Kit (Stratagene). The purified material served as the template in the second QuikChange reaction, which employed only the $His_6$ reverse primer. After 18 cycles, the second reaction was DpnI-digested for one hour at 37° C., and then transformed. The $His_6$-Pfu pol construct was confirmed by both PCR amplification and sequencing using the Big Dye sequencing kit.

Point mutations were introduced into the Pfu pol gene using the QuikChange Site-Directed Mutagenesis Kit (Stratagene). Clones were sequenced to verify incorporation of the desired mutations.

TABLE 1

Activity of partially-purified His-tagged Pfu mutants (Nickel-resin eluates):

| | Polymerase activity | | Exonuclease activity | | Rel. exo/pol |
|---|---|---|---|---|---|
| Mutation | Cpms @ 50 ng (500 ng) | % wild type @ 50 ng* | Cpms (50 ng) | % wild type@ | vs. wt (1.0)$ |
| Partitioning | | | | | |
| S384G | 46920 | 71 | 1425 | ≥100 | 2.3 |
| S384K | 66545 | 100 | 554 | 63 | 0.6 |
| Y385N | 1123 | 2 | 158 | 18 | 10.6 |
| Y385W | 10515 (24519) | 16 | 36 | 4 | 0.3 |
| Y385L | 2383 | 4 | 180 | 21 | 5.7 |
| Y385H | 4276 | 6 | 91 | 10 | 1.6 |
| Y385Q | 386 (5431) | 0.6 | 252 | 29 | 49.2 |
| Y385S | 1095 (4206) | 2 | 578 | 66 | 39.8 |
| Y385F | 80685 (21580) | 100 | 1008 | ≥100 | 0.9 |
| T386E | 48296 | 73 | 263 | 30 | 0.4 |
| T386Y | 47318 | 72 | 1112 | ≥100 | 1.8 |
| T386G | 46289 | 70 | 1011 | ≥100 | 1.6 |
| G387S | 648 | 1 | 169 | 19 | 19.7 |
| G387P | 258 (66) | 0.4 | 500 | 57 | 146.2 |
| G388A | 2560 | 4 | 73 | .008 | 2.2 |
| G388S | 74551 | 100 | 670 | 76 | 0.7 |
| G388P | 1222 | 2 | 202 | 23 | 12.5 |
| F389Y | 43455 (29809) | 66 | 37 | 4 | .06 |
| F389L | 72647 | 100 | 1054 | ≥100 | 1.1 |
| F389V | 30641 | 46 | 614 | 70 | 1.5 |
| F389S | 17998 | 27 | 1335 | ≥100 | 5.6 |
| F389H | 19623 | 30 | 543 | 62 | 2.1 |

| | Polymerase activity | | Exo/pol activity | | |
|---|---|---|---|---|---|
| Polymerase | Cpms @ 5 ng | % wild type @ 5 ng# | Cpms exo-nuclease | Cpms Poly-merase | Rel. exo/pol vs. wt (1.0)& |
| DXXSLYP D405E | 69 (500 ng) | <0.2 | 321 | 0 | >396 |
| Y410F | 10181 | 27 | 698 | 16189 | 5.3 |
| YXDTDS T542P | 27 | .07 | 1105 | 0 | >1364 |
| D543G | 10 | .03 | 704 | 687 | 127 |
| T542P/ D543G | 23 | .06 | 505 | 0 | >623 |

TABLE 1-continued

| | | | | | |
|---|---|---|---|---|---|
| KXY K593T | 155 | .4 | 668 | 0 | >825 |
| Y595S | 6107 | 16 | 1072 | 2684 | 49 |

100% for wt Pfu equals: *66146 cpms; #38014 cpms; @877 cpms
exo/pol for wt Pfu equals: $0.01326; *0.0081

Example 2

Affinity Purification of his-Tagged Pfu DNA Polymerase Mutants

Bacterial Expression of Pfu Mutants.

Plasmid DNA was purified with the StrataPrep® Plasmid Miniprep Kit (Stratagene), and used to transform XL-10 Gold cells. Ampicillin resistant colonies were grown up in 1-5 liters of LB media containing Turbo Amp™ antibiotic (100 μg/μl) at 37° C. with moderate aeration. The cells were collected by centrifugation and stored at −20° C.

Purification (His$_6$ Tag Protocol/Batch Binding Method):

Cells pellets were resuspended in native binding buffer (20 mM phosphate (pH 7.8), 500 mM NaCl). Egg white lysozyme (100 μg/ml) was added and the cells were incubated for 15 minutes on ice. Cell suspensions were subjected to sonication three times with a Bronson Sonifier 250 at a duty cycle of 80% and an output level of 5 for 45 seconds. The suspensions were left on ice to cool between sonication events. The lysate was cleared by centrifugation at 26,890 g. The cleared lysates were added to 5 mls of ProBond Ni resin (Invitrogen), equilibrated in native binding buffer, and the slurry was incubated for two hours with gentle agitation at 4° C. The resin was settled by low speed centrifugation (800×g). The resin was washed three times with 4 ml of native binding buffer (pH 7.8) by resuspending the resin, rocking the slurry for two minutes, and then separating the resin from the supernatant by gravity centrifugation. The resin was then washed in the same fashion with native wash buffer (20 mM phosphate (pH 6.0), 500 mM NaCl). Protein was eluted with two 5-ml additions of 350 mM Imidazole elution buffer (20 mM phosphate, 500 mM NaCl, 350 mM Imidazole (pH 6.0)) by resuspending the resin, rocking the slurry for five minutes, and then separating the resin from the supernatant by gravity centrifugation. Eluted proteins were spin concentrated using Centricon 30 centrifugal filter devices (Amicon). Protein samples were evaluated for size and purity by SDS-PAGE using Tris-Glycine 4-20% acrylamide gradient gels. Gels were stained with silver stain or Sypro Orange (Molecular Probes).

Alternative Expression/Purification:

Alternatively, Pfu mutants were subcloned into the pCAL-n-EK vector (Affinity™ Protein Expression and Purification System) which contains an upstream, in-frame calmodulin binding peptide (CBP) tag for purifying fusion proteins with calmodulin agarose. Plasmid DNA was purified with the StrataPrep® Plasmid Miniprep Kit (Stratagene), and used to transform BL21(DE3) CodonPlus® cells. Ampicillin resistant colonies were grown up in 1-5 liters of LB media containing Turbo Amp™ antibiotic (100 μg/μl) at 30° C. with moderate aeration. When cultures reached an absorbance at OD$_{600}$ of 0.6 to 1.0, the cells were induced with 1 mM IPTG and incubated in the same manner for 2 hours to overnight (16 hours). The cells were collected by centrifugation and stored at −20° C.

Cells pellets were resuspended to an approximate concentration of 0.25 g/ml in buffers identical or similar to calcium binding buffer (50 mM Tris-HCL (pH 8.0), 150 mM NaCl, 1 mM magnesium acetate and 2 mM CaCl). Egg white lysozyme (100 μg/ml) was added and the cells were incubated for 15 minutes on ice. Cell suspensions were subjected to sonication three times with a Bronson Sonifier 250 at a duty cycle of 80% and an output level of 5 for 45 seconds. The suspensions were left on ice to cool between sonication events. The lysate was cleared by centrifugation at 26,890 g.

The cleared lysates were added to 1 ml of calmodulin agarose (CAM agarose), equilibrated in buffer, and the slurry was incubated with gentle agitation at 4° C. After two hours the reactions were centrifuged at 3000 g for 5 minutes to collect the CAM agarose and recombinant protein. The lysate supernatant was removed and the CAM agarose was washed at least once by resuspending the resin in 50 ml of calcium binding buffer followed by collection of the CAM agarose by centrifugation as described above. The CAM agarose was transferred to a disposable 15 ml column, packed, then washed with at least 200 ml of calcium binding buffer. Recombinant proteins were eluted from the column by using a buffer similar or identical to 50 mM Tris-HCl (pH 8.0), 1M NaCl, 2 mM EGTA.

Protein samples were evaluated for size and purity by SDS-PAGE using Tris-Glycine 4-20% acrylamide gradient gels. Gels were stained with silver stain or Sypro Orange (Molecular Probes).

Example 3

Assaying DNA Polymerase and 3'-5' Exonuclease Activities of Pfu DNA Polymerase Mutants Pfu mutant preparations were assayed for DNA polymerase and 3'-5' exonuclease activities as follows.

DNA Polymerase.

DNA polymerase activity was measured by monitoring incorporation of radiolabelled TTP into activated calf thymus DNA. A suitable DNA polymerase reaction cocktail contained: 1×PCR reaction buffer, 200 μM each dATP, dCTP, and dGTP, 195 μM TTP, 5 μM [$^3$H]TTP (NEN #NET-221H, 20.5 Ci/mmole; partially evaporated to remove EtOH), and 250 μg/ml of activated calf thymus DNA (e.g., Pharmacia #27-4575-01). DNA polymerases (wt Pfu or Pfu mutants) were diluted in Pfu storage buffer and 1 μl of each enzyme dilution was added to 10 μl aliquots of polymerase cocktail. Polymerization reactions were conducted in duplicate or triplicate for 30 minutes at 72° C. The extension reactions were quenched on ice, and then 5 μl aliquots were spotted immediately onto DE81 ion-exchange filters (2.3 cm; Whatman #3658323). Unincorporated [$^3$H]TTP was removed by 6 washes with 2×SCC (0.3M NaCl, 30 mM sodium citrate, pH 7.0), followed by a brief wash with 100% ethanol. Incorporated radioactivity was measured by scintillation counting.

Reactions that lack enzyme were set up along with sample incubations to determine "total cpms" (omit filter wash steps) and "minimum cpms" (wash filters as above). Sample cpms were subtracted by minimum cpms to determine "corrected cpms" for each DNA polymerase.

To determine percent (%) activity relative to wild type Pfu, ~50-500 ng of purified Pfu mutants were assayed in a nucleotide incorporation assay, alongside wild type Pfu diluted serially over the linear range of the assay (50-500 pg; 0.003-0.03 U).

Exonuclease Assays.

Exonuclease reactions were performed (in triplicate) by adding 40 aliquots of diluted DNA polymerases (0.25-10 U wt Pfu; 5-200 ng) to 46 μl of reaction cocktail. Reactions were incubated for 1 hour at 72° C. Reactions lacking DNA polymerase were also set up along with sample incubations to determine "total cpms" (no TCA precipitation) and "minimum cpms" (TCA precipitation, see below).

Exonuclease reactions were stopped by transferring the tubes to ice. Sonicated salmon sperm DNA (150 μl; 2.5 mg/ml stock) and TCA (200 μl; 10% stock) were added to all but the "total cpms" tubes. The precipitation reactions were incubated for ≥15 minutes on ice, and then spun in a microcentrifuge at 14,000 rpm for 10 minutes. 200 μl of the supernatant was removed, being careful not to disturb the pellet, and transferred to scintillation fluid (Bio-Safe II™, Research Products International Corp.). The samples were thoroughly mixed by inversion and then counted in a scintillation counter.

To determine percent (%) exonuclease activity relative to wild type Pfu, equivalent amounts of Pfu and purified Pfu mutants (which fall in the linear range of the assay; ~5-200 ng Pfu) are assayed in an exonuclease assay.

Results:

Several Pfu mutants exhibited reductions in DNA polymerase activity compared to wild type Pfu, when tested as partially purified (~50% purity) preparations eluted from nickel resins (Table 1). Pfu mutants showing <10% DNA polymerase activity and at least 10% exonuclease activity include the partitioning domain mutants: Y385QSNLH, G387SP, and G388P and the polymerase domain mutants: D405E, T542P, D543G, and K593T. The initial measurements of % DNA polymerase activity shown in Table 1 was considered as approximate estimates, due to the purity of the protein samples tested and uncertainties as to whether all protein amounts tested were in the linear range of the assay.

Example 4

Purification of Pfu DNA Polymerase Mutants by Conventional Column Chromatography The Pfu K593T and G387P mutants were purified as follows. Cells pellets (12-24 grams) were resuspended in 3 volumes of lysis buffer (buffer A: 50 mM Tris HCl (pH 8.2), 1 mM EDTA, and 10 mM βME). Lysozyme (1 mg/g cells) and PMSF (1 mM) were added and the cells were lysed for 1 hour at 4° C. The cell mixture was sonicated, and the debris removed by centrifugation at 15,000 rpm for 30 minutes (4° C.). Tween 20 and Igepal CA-630 were added to final concentrations of 0.1% and the supernatant was heated at 72° C. for 10 minutes. Heat denatured *E. coli* proteins were then removed by centrifugation at 15,000 rpm for 30 minutes (4° C.).

The supernatant was chromatographed on a Q-Sepharose™ Fast Flow column (~5 ml column), equilibrated in buffer B (buffer A plus 0.1% (v/v) Igepal CA-630, and 0.1% (v/v) Tween 20). Flow-through fractions were collected and then loaded directly onto a P11 Phosphocellulose column (1.6×10 cm), equilibrated in buffer C (same as buffer B, except pH 7.5). The column was washed and then eluted with a 0-0.7M KCl gradient/Buffer C. Fractions containing Pfu DNA polymerase mutants (95 kD by SDS-PAGE) were dialyzed overnight against buffer D (50 mM Tris HCl (pH 7.5), 5 mM βME, 5% (v/v) glycerol, 0.2% (v/v) Igepal CA-630, 0.2% (v/v) Tween 20, and 0.5M NaCl) and then applied to a Hydroxyapatite column (1.0×1.3 cm; ~1 ml), equilibrated in buffer D. The column was washed and Pfu DNA polymerase mutants were eluted with buffer D2 containing 400 mM KPO₄, (pH 7.5), 5 mM βME, 5% (v/v) glycerol, 0.2% (v/v) Igepal CA-630, 0.2% (v/v) Tween 20, and 0.5 M NaCl. Purified proteins were spin concentrated using Centricon YM30 devices, and exchanged into Pfu final dialysis buffer (50 mM Tris-HCl (pH 8.2), 0.1 mM EDTA, 1 mM dithiothreitol (DTT), 50% (v/v) glycerol, 0.1% (v/v) Igepal CA-630, and 0.1% (v/v) Tween 20).

Results:

His-tagged Pfu G387P and K593T mutants were purified by ion exchange/hydroxyappetite (IE/HA) chromatography. The purified protein preps were analyzed by SDS-PAGE and determined to be of ≥95% purity. The IE/HA purified mutants were tested in a nucleotide incorporation assay to more precisely quantify percent remaining DNA polymerase activity. As shown in Table 2, the Pfu G387P mutant exhibits no significant DNA polymerase activity (<100 cpms above background) when 0.2 μg to 1.2 μg of protein was assayed. These results indicate that the Pfu G387P mutant exhibits <0.01% (<100/16661×25/1200=0.00013) of the DNA polymerase activity exhibited by wild type Pfu DNA polymerase. In comparison, the Pfu K593T mutant retains approximately 1-2% of the DNA polymerase activity of wild type Pfu.

TABLE 2

Residual Polymerase Activity in IE/HA Purified Pfu Mutant Preps:

| Pfu DNA Polymerase | Amount. Assayed (ng) | Corrected cpms | Relative (%) Polymerase Activity | Mean Relative Polymerase Activity |
|---|---|---|---|---|
| Wild type | 25 | 16,661 | 100 | 100 |
| G387P | 240 | 42 | 0.026 | Cpms not significantly (<100 cpms) above background; therefore, assume <100/16661 × 25/1200 = <0.01% |
|  | 600 | 0 | — |  |
|  | 1200 | 16 | 0.002 |  |
| K593T | 80 | 1228 | 2.3 | 1.8 |
|  | 200 | 1774 | 1.3 |  |

Example 5

Verifying the Presence of Proofreading Activity in Pfu Mutants Under PCR Conditions A qualitative assay was used to verify that Pfu mutants retained 3'-5' exonuclease activity under PCR conditions. In this assay, the 900 bp HαlAT target is amplified with exo⁻ Pfu DNA polymerase (2.5 U/50 μl) using a forward primer containing a 3' dG, which produces a dG/dG mismatch upon annealing to the DNA template. The amplicon is amplified from human genomic DNA using the forward primer: 5'-GAG.GAG.AGC.AGG.AAA.GGT.GGA.AG-3' [SEQ ID NO. 8] (100 ng/50 μl rxn) and the reverse primer: 5'-GAG.GTA.CAG.GGT.TGA.GGC.TACT.G-3' [SEQ ID NO. 9] (100 ng/50 μl rxn). Amplification is carried out in the absence or presence of varying amounts of Pfu mutants (200 ng to 3.6 μg) on a Perkin/Elmer 9600 thermal cycler with the following program: (1 cycle) 95° C. for 2.5 minutes; (30 cycles) 95° C. for 40 seconds, 61° C. for 10 seconds, 72° C. for 2.5 minutes; (1 cycle) 72° C. for 7 minutes. In the absence of proofreading activity, exo⁻ Pfu produces low yields of product, presumably because the enzyme can not efficiently extend a dG/dG mismatch. In the presence of Pfu mutants with proofreading activity, the 3' dG should be excised from the primer, thereby allowing exo⁻ Pfu to amplify the target in high yields. This PCR assay was used to verify that Pfu mutants tested in fidelity assays retained sufficient proofreading activity under PCR conditions to excise mismatched PCR primers. Moreover, the assay allowed us to determine the range of protein concentrations that could be added to PCR reactions without inhibition of amplification.

Results:

As shown in FIG. 1, amplifications conducted with exo⁻ Pfu alone produced low yields of product due to poor extension of the dG/dG mismatch. Product yields were significantly higher in the presence of the Pfu G387P and K593T mutants (125-500 ng), presumably because these mutants excise the 3' dG from the primer, thereby allowing exo⁻ Pfu to efficiently amplify the target. Additional experiments showed that the polymerase deficient Pfu G387P and K593T mutants were unable to amplify the target in the absence of exo⁻ Pfu (or wild type Pfu).

TABLE 3

Example 6. Range Of Ratios Of Exonuclease And Polymerase Activities To Use In Blends
Enzyme blend

| Polymerase proficient enzyme | | Polymerase deficient enzyme | | |
| --- | --- | --- | --- | --- |
| Polymerase | Amount Polymerase (3'-5' Exo) | Pfu Mutant | Range of Amounts Tested that Produce Highest Fidelity and Yield | |
| | | | Ng | Polymerase (U)@ | 3'-5' Exo (U)@ |
| Pfu/ Pfu Turbo* | 2.5-5 U (0.05-.09 U exo) | G387P | 600& 1800 3600 | <0.003 <0.009 <0.018 | 0.56& 1.68 3.36 |
| Taq# | 2.5 U (0) | G387P | 600& 3600$ | <0.003 <0.018 | 0.56& 3.36$ |

*600 ng-3600 ng of Pfu G387P provided similar improvements in the accuracy of Pfu; 1800 ng was the highest amount that could be added with no inhibition of any PCR reaction tested (up to 17 kb); at least one PCR system amplified successfully in the presence of 3600 ng Pfu G387P
600 ng of Pfu G387P increased accuracy of Taq by 5-fold, while 3600 ng increased accuracy by 8-fold; several targets <5 kb successfully amplified in the presence of 3600 ng of Pfu G387P; maximum amount of Pfu G387P that can be used in PCR may be >3600 ng.
&minimum amount could be lower; haven't tested amounts <600 ng in a fidelity assay
$maximum amount could be higher; haven't tested amounts <3600 ng in PCR
@calculations assume 50-100 ng of Pfu equals 2.5 U DNA polymerase activity (specific activity is 2.6 × 10³ U/mg; measured at 72° C. using activated calf thymus DNA in a universal assay buffer (50 mM Tris-HCl (pH 8.0), 5 mM MgCl₂, 1 mM DTT, and 50 µg/ml BSA)) and that the specific exonuclease activity of Pfu is 935 U/mg (measured at 72° in the absence of dNTPs using double-stranded Pal I-digested λ DNA in a universal assay buffer (70 mM Tris HCl (pH 8.8), 2 mM MgCl₂, 0.1% Triton-X, and 100 µg/ml BSA)).

Example 7

PCR Amplification with Pfu or Taq DNA Polymerase Blends Containing Pfu Mutants

Pfu Blends.

PCR reactions were conducted under standard conditions in cloned Pfu PCR buffer (10 mM KCl, 10 mM (NH₄)₂SO₄, 20 mM Tris HCl (pH 8.8), 2 mM Mg SO₄, 0.1% Triton X-100, and 100 µg/ml BSA) with 2.5-5 U PfuTurbo DNA polymerase (2.5 U/µl cloned Pfu DNA polymerase plus 1 U/µl native or 2 U/µl cloned *Pyrococcus furiosus* dUTPase (PEF)) and varying concentrations of polymerase deficient Pfu mutants (e.g., 0.2 to 3.6 µg). For genomic targets 0.3-9 kb in length, PCR reactions contained 2.5 U Pfu Turbo DNA polymerase, 100 ng of human genomic DNA, 200 µM each dNTP, and 100 ng of each primer. For genomic targets 11.9 kb and 17 kb in length, PCR reactions contained 5 U PfuTurbo DNA polymerase, 250 ng of human genomic DNA, 500 µM each dNTP, and 200 ng of each primer.

Taq Blends.

PCR reactions were conducted under standard conditions in Herculase PCR buffer (50 mM Tricine (pH 9.1), 8 mM (NH₄)₂SO₄, 2.3 mM MgCl₂, 0.1% Tween-20, and 75 µg/ml BSA) with 2.5 U cloned Taq DNA polymerase, 1 U of native or 2 U cloned *Pyrococcus furiosus* dUTPase (PEF)), and varying concentrations of polymerase deficient Pfu mutants.

TABLE 4

| Cycling Conditions: | | |
| --- | --- | --- |
| Target size (kb) | Target gene | Cycling Parameters |
| 0.3 | Aldolase B | (1 cycle) 95° C. 2 min (30 cycles) 95° C. 40 sec, 58° C. 30 sec, 72° C. 1 min (1 cycle) 72° C. 7 min |
| 0.9 | HαlAT | (1 cycle) 95° C. 2 min (30 cycles) 95° C. 40 sec, 58° C. 30 sec, 72° C. 1 min (1 cycle) 72° C. 7 min |
| 2.3 | Pfu pol (5 ng plasmid DNA) | (1 cycle) 95° C. 2 min (30 cycles) 95° C. 40 sec, 58° C. 30 sec, 72° C. 3 min (1 cycle) 72° C. 7 min |
| 2.6 | HαlAT | (1 cycle) 95° C. 2 min (30 cycles) 95° C. 40 sec, 58° C. 30 sec, 72° C. 3 min (1 cycle) 72° C. 7 min |
| 4 | HαlAT | (1 cycle) 95° C. 2 min (30 cycles) 95°C. 40 sec, 54° C. 30 sec, 72° C. 5 min (1 cycle) 72° C. 7 min |
| 9.3 | HαlAT | (1 cycle) 95° C. 2 min (30 cycles) 95° C. 40 sec, 58° C. 30 sec, 72° C. 18 min (1 cycle) 72° C. 10 min |
| 11.9 | HαlAT | (1 cycle) 95° C. 2 min (30 cycles) 95° C. 40 sec, 58° C. 30 sec, 72° C. 24 min (1 cycle) 72° C. 10 min |
| 17 | β globin | (one cycle) 92° C. 2 min (10 cycles) 92° C. 10 sec, 63° C. 30 sec, 68° C. 30 min (20 cycles) 92° C. 10 sec, 63° C. 30 sec, 68° C. 30 min (plus 10 sec/cycle) (one cycle) 68° C. 10 min |

Results (Pfu Blend PCR Performance):

As shown in FIG. 2, adding 600 ng of the Pfu G387P mutant to Pfu (in the presence of PEF/dUTPase), has minimal effects on PCR product yield. Additional experiments have shown that up to 1800 ng of the Pfu G387P mutant can be added without significantly reducing PCR product yield.

Results (Taq Blend PCR Performance):

As shown in FIG. 3, adding the Pfu G387P mutant to Taq, in the presence of PEF/dUTPase, significantly increases PCR product yields when amplifications are performed in a reaction buffer that supports the activity of both Taq and Pfu DNA polymerases. One such buffer is the Herculase PCR buffer, which was developed specifically for Herculase Enhanced DNA polymerase (3.33 U/µl cloned Pfu, 1.67 U/µl cloned Taq, 2 U/µl cloned *Pyrococcus furiosus* dUTPase). In the example shown in FIG. 3, a 4 kb target could not be amplified in high yield using Taq alone in Taq, Pfu, or Herculase PCR buffer. In the presence of the Pfu G387P mutant (and dUTPase), the 4 kb target could be amplified in cloned Pfu buffer (moderate yield) but not Taq buffer, consistent with the buffer preferences of the Pfu G387P mutant. Other experiments have shown that the Pfu G387P mutant inhibits PCR reactions carried out with Taq in Taq PCR buffer, suggesting that the Pfu G387P mutant binds the 3' ends of PCR products without excising mismatches and dissociating (due to inactivity in Taq buffer), and blocks further product extension. As expected, highest product yields are obtained with Taq plus Pfu G387P blends in the presence of Herculase buffer, since both enzymes are highly active in this particular buffer. The Pfu G387P mutant is thought to enhance the yields of Taq PCR reactions (in buffers where Pfu is active) by excising mispairs that would otherwise stall Taq.

Example 8

Measuring the Fidelity of DNA Polymerase Blends Containing Pfu DNA Polymerase Mutants The error rates of Pfu and Taq blends containing the Pfu G387P and K593T mutants were tested in the lacI PCR fidelity assay described in Cline, J., Braman, J. C., and Hogrefe, H. H. (96) NAR 24:3546-3551. Briefly, a 1.9 kb fragment encoding the lacIOlacZα target gene was amplified from pPRIAZ plasmid DNA using 2.5 U PfuTurbo in cloned Pfu PCR buffer or 2.5 U Taq in Taq or Herculase PCR buffer. Varying amounts of the Pfu G387P (600-3600 ng) and K593T (200-1200 ng) mutants were added to certain reactions. For comparative purposes, the lacI target was also amplified with Pfx (*Thermococcus* sp. KOD DNA polymerase; Invitrogen) and Tgo (*Thermococcus gorgonarius* DNA polymerase; Roche) using the manufacturers' recommended PCR buffer. The lacI-containing PCR products were then cloned into lambda GT10 arms, and the percentage of lacI mutants (MF, mutation frequency) was determined in a color screening assay, as described (Lundberg, K. S., Shoemaker, D. D., Adams, M. W. W., Short, J. M., Sorge, J. A., and Mathur, E. J. (1991) Gene 180:1-8). Error rates are expressed as mutation frequency per by per duplication (MF/bp/d), where by is the number of detectable sites in the lacI gene sequence (349) and d is the number of effective target doublings. For each enzyme, at least two independent PCR amplifications were performed.

Error rate measurements have shown that Pfu and PfuTurbo DNA polymerases exhibit an average error rate which is ~2-fold lower than that of Vent, Deep Vent, and Pfx (KOD) DNA polymerases, 3 to 6-fold lower than those of DNA polymerase mixtures, and 6- to 12-fold lower than that of Taq DNA polymerase.

Results (Pfu Blend):

As shown Table 5, adding 600 ng-3600 ng of the IE/HA-purified Pfu G387G mutant reduced the error rate of Pfu-Turbo DNA polymerase by 3.2 to 3.5-fold (assay 1) and by 1.8 to 2.8-fold (assay 2) in two independent fidelity assays. Under these conditions, the Pfu G387G mutant was present at approximately a 12-fold (600 ng; <0.003 U polymerase activity; 0.56 U exonuclease activity) to 72-fold (3600 ng; <0.018 U polymerase activity; 3.4 U exonuclease activity) molar excess over wild type Pfu. These assumptions were based upon 2.5 U Pfu equaling ~50 ng protein, the Pfu G387G mutant exhibiting <0.01% DNA polymerase activity, and wt Pfu exhibiting a specific activity of 935 U/mg). As discussed in Example 5, up to 1800 ng of the IE/HA-purified Pfu G387G mutant can be added to PCR reactions without significantly reducing PCR product yield.

In comparison, adding 200 ng of the Pfu K593T mutant reduced the error rate of PfuTurbo DNA polymerase slightly (40%), while the addition of 600 ng and 1200 ng (~12 to 24-fold excess over Pfu) increased error rate by 2.8- and 7.3-fold, respectively. At 600-1200 ng, approximately 0.5-1 U of additional DNA polymerase activity is added to the PCR reaction (Pfu K593T mutant exhibits 1-2% polymerase activity). The K593T mutation significantly increases the misincorporation or mispair extension rate of Pfu, and when added at high amounts (corresponding to ≥0.5 U), the Pfu K593T mutant dramatically increases the error rate of wild type Pfu.

Results (Taq Blend):

As shown Table 6, adding 600 ng and 3600 ng of the Pfu G387G mutant reduced the error rate of Taq DNA polymerase by 5.1- and 8.3-fold, respectively. Therefore, the error rate of Taq in the presence of the Pfu G387G mutant, can equal the error rate of Pfu alone.

TABLE 5

Fidelity of Pfu Blends Containing IE/HA Purified Pfu Mutants:

| PCR Enzyme | His-Pfu Mutant | Mutant Amount | | Error rate* ($\times 10^{-6}$) | | Mean Relative Accuracy (Pfu) |
|---|---|---|---|---|---|---|
| | | ng (×Pfu) | pol units | Assay 1 | Assay 2 | |
| Pfu | none | — | — | 5.55 | 3.60 | 1.0 |
| | G387P | 600 (12×) | <0.003 | 1.60 | 2.06 | 2.6 |
| | | 1800 (36×) | <0.009 | 1.65 | 1.18 | 3.2 |
| | | 2400 (48×) | <0.012 | Nd | 1.30 | 2.8 |
| | | 3600 (72×) | <0.018 | 1.75 | nd | 3.2 |
| | K593T | 200 (4×) | 0.18 | 3.9 | nd | 1.4 |
| | | 600 (12×) | 0.54 | 15.7 | nd | 0.4 |
| | | 1200 (24×) | 1.1 | 40.3 | nd | 0.1 |
| Tgo | none | — | — | nd | 6.10 | 0.6 |
| Taq | none | — | — | 34.7 | 19.0 | 0.2 |

*mean of duplicate measurements

TABLE 6

Fidelity of Taq Blends Containing IE/HA Purified Pfu Mutants:

| PCR Enzyme | His-Pfu Mutant | Mutant Amount (ng) | Error rate* ($\times 10^{-6}$) | Relative Accuracy (Pfu) |
|---|---|---|---|---|
| Taq | none | — | 34.7 | 0.16 |
| | G387P | 600 | 6.8 | 0.82 |
| | | 3600 | 4.2 | 1.32 |
| | K593T | 200 | 37.0 | 0.15 |
| Pfu | none | — | 5.6 | 1.0 |
| | G387P | 600 | 1.60 | 3.47 |
| | | 3600 | 1.75 | 3.17 |
| | K593T | 200 | 3.90 | 1.42 |

*mean of duplicate measurements

Example 9

Determining the TA Cloning Efficiencies of PCR Products Amplified with Taq in the Presence of Pfu Mutants To determine the effects of polymerase deficient Pfu mutants on the terminal transferase activity of Taq, we amplified a series of amplicons with Taq in the absence of the Pfu G387P mutant (in Taq PCR buffer) or in the presence of the Pfu G387P mutant (in Herculase PCR buffer). Similar amplifications were performed using PfuTurbo and Herculase in their recommended PCR buffers. PCR product yields were quantified by analyzing the products on 1% agarose gels, stained with SYBR gold. The same amount of each PCR product was added to 1 μl of the pCR 2.1-TOPO vector (Invitrogen) in a final reaction volume of 6 μl, according the manual for the TOPO TA Cloning Kit (#K4500-01). The reactions were incubated for 5 minutes at room temperature, and then transferred to ice. The reactions were transformed into One-Shot cells (Invitrogen), according to the manufacture's recommendations. Aliquots of each transformation were plated on amplicillin/IPTG/X-gal plates, prepared as described in the Invitrogen TOPO TA Cloning manual. The frequency of clones containing the desired insert (% cloning efficiency) was quantified as the number of (white colonies)/(total number of colonies plated).

Results:

As shown in Table 7, PCR products amplified with Taq in the presence of the Pfu G387P mutant are cloned into the TOPO TA cloning vector as efficiently as PCR products amplified with Taq alone. In contrast, PCR products amplified with PfuTurbo DNA polymerase are cloned into the TOPO TA cloning vector much less efficiently, presumably due to the lack of 3' dAs. As discussed in Example 7, PCR products amplified with Taq blends containing the Pfu G387P mutant, should also exhibit fewer errors (5- to 8-fold less) compared to PCR products amplified with Taq alone. Therefore, Taq blends containing the Pfu G387P mutant should be useful to researchers using TA cloning methods, but desiring high-fidelity amplication of inserts. The high TA cloning efficiencies obtained in the presence of the Pfu G387P mutant indicates that 3' dAs added by Taq during PCR are unexpectedly resistant to exonucleolytic degradation. Presumably, Pfu DNA polymerase is not very efficient at excising 3' dA residues from double-stranded PCR products in the presence of nucleotides.

TABLE 7

| TopoTA Cloning Efficiencies: | | | |
|---|---|---|---|
| PCR Product (bp) | PCR enzyme/blend | | Cloning efficiency (%) |
| | DNA polymerase | Pol⁻ Pfu mutant | |
| | | mutant | amount (µg) | |
| 900 | Taq | none | — | 89 |
| | | G387P | 0.6 | 80 |
| | | G387P | 3.6 | 89 |
| | Pfu | none | — | 8 |

TABLE 7-continued

| TopoTA Cloning Efficiencies: | | | |
|---|---|---|---|
| PCR Product (bp) | PCR enzyme/blend | | Cloning efficiency (%) |
| | DNA polymerase | Pol⁻ Pfu mutant | |
| | | mutant | amount (µg) | |
| 300 | Taq | none | — | 69 |
| | | G387P | 0.6 | 73 |
| | | G387P | 3.6 | 78 |
| | Pfu | none | — | 33 |
| | Herculase | None | — | 46 |
| 2300 | Taq | None | — | 83 |
| | | G387P | 0.6 | 88 |
| | | G387P | 3.6 | 92 |
| | Pfu | None | — | 22 |
| | Herculase | None | — | 85 |

Other Embodiments

The foregoing examples demonstrate experiments performed and contemplated by the present inventors in making and carrying out the invention. It is believed that these examples include a disclosure of techniques which serve to both apprise the art of the practice of the invention and to demonstrate its usefulness. It will be appreciated by those of skill in the art that the techniques and embodiments disclosed herein are preferred embodiments only that in general numerous equivalent methods and techniques may be employed to achieve the same result.

All of the references identified hereinabove, are hereby expressly incorporated herein by reference to the extent that they describe, set forth, provide a basis for or enable compositions and/or methods which may be important to the practice of one or more embodiments of the present inventions.

The invention claimed is:

1. An enzyme mixture comprising a first enzyme and a second enzyme, wherein said first enzyme is a DNA polymerase or reverse transcriptase, and said second enzyme is the wild type Pfu DNA polymerase comprising the amino acid sequence of SEQ ID NO. 12, except that it is mutated at an amino acid position selected from the group consisting of: Y410, D543, K593, G387, G388, and the following amino acid substitutions: Y385N, Y385W, Y385L, Y385H, Y385Q, and Y385S, and wherein said second enzyme possesses reduced 3'-5' exonuclease activity and reduced 5'-3' DNA polymerization activity as compared to the wild type Pfu DNA polymerase.

2. The enzyme mixture of claim 1, wherein said first enzyme is selected from the group consisting of: Taq DNA polymerase, Tth DNA polymerase, U1Tma DNA polymerase, Tli DNA polymerase (Vent DNA polymerase), Pwo DNA polymerase, Tgo DNA polymerase, Pfu DNA polymerase, KOD DNA polymerase, JDF-3 DNA polymerase having the sequence shown in SEQ ID NO. 10, PGB-D DNA polymerase (Deep Vent DNA polymerase) and DP1/DP2 DNA polymerase.

3. The enzyme mixture of claim 1, wherein said Pfu DNA polymerase mutations are one or more amino acid substitutions selected from the group consisting of: Y410F, D543G, K593T, Y385Q, Y385S, Y385N, Y385L, Y385H, G387S, G387P, and G388P.

4. The enzyme mixture of claim 1, further comprising a PCR enhancing factor and/or an additive.

5. A kit comprising a first enzyme, a second enzyme, and packaging material therefor, wherein said first enzyme is a DNA polymerase or reverse transcriptase, and said second enzyme is the wild type Pfu DNA polymerase comprising the amino acid sequence of SEQ ID NO. 12, except that it is mutated at an amino acid position selected from the group consisting of: Y410, D543, K593, G387, and G388, G388, and the following amino acid substitutions: Y385N, Y385W, Y385L, Y385H, Y385Q, and Y385S, and wherein said second enzyme possesses reduced 3'-5' exonuclease activity and reduced 5'-3' DNA polymerization activity as compared to the wild type Pfu DNA polymerase.

6. The kit of claim 5, wherein said first enzyme is selected from the group consisting of: Taq DNA polymerase, Tth DNA polymerase, U1Tma DNA polymerase, Tli DNA polymerase (Vent DNA polymerase), Pwo DNA polymerase, Tgo DNA polymerase, Pfu DNA polymerase, KOD DNA polymerase, JDF-3 DNA polymerase having the sequence shown in SEQ ID NO. 10, PGB-D DNA polymerase (Deep Vent DNA polymerase) and DP1/DP2 DNA polymerase.

7. The kit of claim 5, further comprising one or more components selected from the group consisting of: a deoxynucleotide, a reaction buffer, a PCR enhancing factor and/or an additive, a control DNA template and a control primer.

8. The kit of claim 5, wherein said Pfu DNA polymerase mutations are one or more amino acid substitutions selected from the group consisting of: Y410F, D543G, K593T, Y385Q, Y385S, Y385N, Y385L, Y385H, G387S, G387P, and G388P.

9. A method for DNA synthesis comprising:
(a) providing said enzyme mixture of claim 1; and
(b) contacting said enzyme mixture with a nucleic acid template, wherein said enzyme mixture permits DNA synthesis.

10. The method of claim 9, wherein said nucleic acid template is a DNA molecule.

11. The method of claim 9, wherein said first enzyme is selected from the group consisting of: Taq DNA polymerase, Tth DNA polymerase, U1Tma DNA polymerase, Tli DNA polymerase, Pfu DNA polymerase, KOD DNA polymerase, JDF-3 DNA polymerase, PGB-D DNA polymerase and DP1/DP2 DNA polymerase.

12. A method for DNA synthesis comprising:
    (a) providing said enzyme mixture of claim 1, and
    (b) contacting said enzyme mixture with a nucleic acid template, wherein said enzyme mixture permits DNA synthesis.

13. The method of claim 9, wherein said Pfu DNA polymerase mutations are one or more amino acid substitutions selected from the group consisting of: D405E, Y410F, D543G, K593T, Y385Q, Y385S, Y385N, Y385L, Y385H, G387S, G387P, and G388P.

14. An enzyme mixture comprising a first enzyme and a second enzyme, wherein said first enzyme is Taq DNA polymerase, and said second enzyme is the wild type Pfu DNA polymerase comprising the amino acid sequence of SEQ ID NO. 12, except that it is mutated at an amino acid position selected from the group consisting of: Y410, D543, K593, G387, G388, and the following amino acid substitutions: Y385N, Y385W, Y385L, Y385H, Y385Q, and Y385S, and wherein said second enzyme possesses reduced 3'-5' exonuclease activity and reduced 5'-3' DNA polymerization activity as compared to the wild type Pfu DNA polymerase.

15. A method for TA cloning of DNA synthesis product comprising:
    (a) providing the enzyme mixture of claim 14;
    (b) contacting said enzyme mixture with a nucleic acid template, wherein said enzyme mixture permits DNA synthesis to generate a synthesized DNA product; and
    (c) inserting said synthesized DNA product into a TA cloning vector.

16. The method of claim 9, 12 or 15, wherein said reaction mixture further comprises a PCR enhancing factor and/or an additive.

17. The method of claim 12 or 15, wherein said Pfu DNA polymerase mutations are one or more amino acid substitutions selected from the group consisting of: D405E, Y410F, D543G, K593T, Y385Q, Y385S, Y385N, Y385L, Y385H, G387S, G387P, and G388P.

18. The enzyme mixture of claim 14, wherein said Pfu DNA polymerase mutations are one or more amino acid substitutions selected from the group consisting of: Y410F, D543G, K593T, Y385Q, Y385S, Y385N, Y385L, Y385H, G387S, G387P, and G388P.

19. The enzyme mixture of claim 14, wherein said Pfu DNA polymerase is mutated at amino acid position G387.

20. The enzyme mixture of claim 14, wherein said Pfu DNA polymerase is mutated at amino acid position G387 and the resulting amino acid substitution is G387P.

21. An enzyme mixture comprising a first enzyme and a second enzyme, wherein said first enzyme is KOD DNA polymerase, and said second enzyme is the wild type Pfu DNA polymerase comprising the amino acid sequence of SEQ ID NO. 12, except that it is mutated at an amino acid position selected from the group consisting of: D405, Y410, D543, K593, G387, G388, and the following amino acid substitutions: Y385N, Y385W, Y385L, Y385H, Y385Q, and Y385S, and wherein said second enzyme possesses reduced 3'-5' exonuclease activity and reduced 5'-3' DNA polymerization activity as compared to the wild type Pfu DNA polymerase.

22. The enzyme mixture of claim 21, wherein said Pfu DNA polymerase mutations are one or more amino acid substitutions selected from the group consisting of: D405E, Y410F, D543G, K593T, Y385Q, Y385S, Y385N, Y385L, Y385H, G387S, G387P and G388P.

23. The enzyme mixture of claim 21, wherein said Pfu DNA polymerase is mutated at amino acid position G387.

24. The enzyme mixture of claim 21, wherein said Pfu DNA polymerase is mutated at amino acid position G387 and the resulting amino acid substitution is G387P.

25. An enzyme mixture comprising a first enzyme and a second enzyme, wherein said first enzyme is a JDF-3 DNA polymerase having the sequence shown in SEQ ID NO. 10, and said second enzyme is the wild type Pfu DNA polymerase comprising the amino acid sequence of SEQ ID NO. 12, except that it is mutated at an amino acid position selected from the group consisting of: D405, Y410, D543, K593, G387, G388, and the following amino acid substitutions: Y385N, Y385W, Y385L, Y385H, Y385Q, and Y385S, and wherein said second enzyme possesses reduced 3'-5' exonuclease activity and reduced 5'-3' DNA polymerization activity as compared to the wild type Pfu DNA polymerase.

26. The enzyme mixture of claim 25, wherein said Pfu DNA polymerase mutations are one or more amino acid substitutions selected from the group consisting of: D405E, Y410F, D543G, K593T, Y385Q, Y385S, Y385N, Y385L, Y385H, G387S, G387P and G388P.

27. The enzyme mixture of claim 25, wherein said Pfu DNA polymerase is mutated at amino acid position G387.

28. The enzyme mixture of claim 25, wherein said Pfu DNA polymerase is mutated at amino acid position G387 and the resulting amino acid substitution is G387P.

29. A kit comprising a first enzyme and a second enzyme, wherein said first enzyme is a Taq DNA polymerase, and said second enzyme is the wild type Pfu DNA polymerase comprising the amino acid sequence of SEQ ID NO. 12, except that it is mutated at an amino acid selected from the group consisting of Y410, D543, K593, G387, G388, and the following amino acid substitutions: Y385N, Y385W, Y385L, Y385H, Y385Q, and Y385S, or combinations thereof, and packaging material therefor, and wherein said second enzyme possesses reduced 3'-5' exonuclease activity and reduced 5'-3' DNA polymerization activity as compared to the wild type Pfu DNA polymerase.

30. A kit comprising a first enzyme and a second enzyme, wherein said first enzyme is a KOD DNA polymerase, and said second enzyme is the wild type Pfu DNA polymerase comprising the amino acid sequence of SEQ ID NO. 12, except that it is mutated at an amino acid selected from the group consisting of D405, Y410, D543, K593, G387, G388, and the following amino acid substitutions: Y385N, Y385W, Y385L, Y385H, Y385Q, and Y385S, or combinations thereof, and packaging material therefor, and wherein said second enzyme possesses reduced 3'-5' exonuclease activity and reduced 5'-3' DNA polymerization activity as compared to the wild type Pfu DNA polymerase.

31. A kit comprising a first enzyme and a second enzyme, wherein said first enzyme is a JDF-3 DNA polymerase having the sequence shown in SEQ ID NO. 10, and said second enzyme is the wild type Pfu DNA polymerase comprising the amino acid sequence of SEQ ID NO. 12, except that it is mutated at an amino acid selected from the group consisting of: D405, Y410, D543, K593, G387, G388, and the following amino acid substitutions: Y385N, Y385W, Y385L, Y385H, Y385Q, and Y385S, or combinations thereof, and packaging material therefor, and wherein said second enzyme possesses reduced 3'-5' exonuclease activity and reduced 5'-3' DNA polymerization activity as compared to the wild type Pfu DNA polymerase.

32. The kit of claim 29, 30, or 31, wherein said kit further comprises a reagent selected from the group consisting of: dNTPs, reaction buffer, primer, and DNA enhancing factor.

33. An enzyme mixture comprising a first enzyme and a second enzyme, wherein said first enzyme is a DNA polymerase or reverse transcriptase, and said second enzyme is the wild type Pfu DNA polymerase comprising the amino acid sequence of SEQ ID NO. 12, except that it is mutated at an amino acid position selected from the group consisting of: T542 and Y595, or comprises a Y385F substitution, and wherein said second enzyme possesses 3'-5' exonuclease activity and reduced 5'-3' DNA polymerization activity as compared to the wild type Pfu DNA polymerase.

* * * * *

UNITED STATES PATENT AND TRADEMARK OFFICE
CERTIFICATE OF CORRECTION

PATENT NO. : 9,181,534 B1
APPLICATION NO. : 10/035091
DATED : November 10, 2015
INVENTOR(S) : Holly Hogrefe et al.

It is certified that error appears in the above-identified patent and that said Letters Patent is hereby corrected as shown below:

On the Title page, in item (75), in column 1, in "Inventors", line 1, delete "San Deigo," and insert -- San Diego, --, therefor.

In The Specification

In column 4, line 2, delete "of" and insert -- of: --, therefor.

In column 6, line 18, delete "polymerse," and insert -- polymerase, --, therefor.

In column 7, line 31-32, delete "Bacteoriol," and insert -- Bacteriol, --, therefor.

In column 7, line 39, delete "DNA.polymerase" and insert -- DNA polymerase --, therefor.

In column 8, line 10, delete "proof reading" and insert -- proofreading --, therefor.

In column 13-14, line 40, delete "agagccgaag" and insert -- cgagccgaag --, therefor.

In column 13-14, line 47, delete "gaatacgaga" and insert -- gcctacgaga --, therefor.

In column 15-16, line 3, delete "tcaatcatcc" and insert -- tcaatcataa --, therefor.

In column 17, line 29, delete "proof reading" and insert -- proofreading --, therefor.

In column 17, line 42, delete "horikoshi" and insert -- horikoshii --, therefor.

In column 18, line 20, delete "Solfolobus" and insert -- Sulfolobus --, therefor.

In column 20, line 22, delete "ul" and insert -- µl --, therefor.

In column 20, line 25, delete "ul" and insert -- µl --, therefor.

In column 20, line 50, delete "form" and insert -- from --, therefor.

In column 30, line 21, delete "ration" and insert -- ratio --, therefor.

In column 34, line 61, delete "Trimethlamine" and insert -- Trimethylamine --, therefor.

In column 35, line 41, delete "Recusive" and insert -- Recursive --, therefor.

In column 35, line 66, delete "Y" and insert -- 3' --, therefor.

In column 42, line 65, delete "40" and insert -- 4 µl --, therefor.

Signed and Sealed this
Twenty-ninth Day of March, 2016

Michelle K. Lee
*Director of the United States Patent and Trademark Office*

CERTIFICATE OF CORRECTION (continued)
U.S. Pat. No. 9,181,534 B1

In column 44, line 6, delete "exchange/hydroxyappetite (IE/HA) chromotography." and insert -- exchange/hydroxyapatite (IE/HA) chromatography. --, therefor.

In column 47, line 28, delete "by per duplication (MF/bp/d), where by" and insert -- bp per duplication (MF/bp/d), where bp --, therefor.

In column 48, line 63, delete "amplicillin" and insert -- ampicillin --, therefor.

In column 49, line 15, delete "amplication" and insert -- amplification --, therefor.

In The Claims

In column 64, line 42-43, in claim 5, delete "G387, and G388, G388, and the" and insert -- G387, G388, and the --, therefor.

SEQUENCE LISTING

```
<160> NUMBER OF SEQ ID NOS: 12

<210> SEQ ID NO 1
<211> LENGTH: 7
<212> TYPE: PRT
<213> ORGANISM: Artificial Sequence
<220> FEATURE:
<223> OTHER INFORMATION: Description of Artificial Sequence: Synthetic
      conserved domain peptide
<220> FEATURE:
<221> NAME/KEY: MOD_RES
<222> LOCATION: (2)..(3)
<223> OTHER INFORMATION: Any amino acid

<400> SEQUENCE: 1

Asp Xaa Xaa Ser Leu Tyr Pro
1               5

<210> SEQ ID NO 2
<211> LENGTH: 9
<212> TYPE: PRT
<213> ORGANISM: Artificial Sequence
<220> FEATURE:
<223> OTHER INFORMATION: Description of Artificial Sequence: Synthetic
      conserved domain peptide
<220> FEATURE:
<221> NAME/KEY: MOD_RES
<222> LOCATION: (2)..(4)
<223> OTHER INFORMATION: Any amino acid
<220> FEATURE:
<221> NAME/KEY: MOD_RES
<222> LOCATION: (7)..(7)
```

<223> OTHER INFORMATION: Any amino acid

<400> SEQUENCE: 2

Lys Xaa Xaa Xaa Asn Ser Xaa Tyr Gly
1               5

<210> SEQ ID NO 3
<211> LENGTH: 5
<212> TYPE: PRT
<213> ORGANISM: Artificial Sequence
<220> FEATURE:
<223> OTHER INFORMATION: Description of Artificial Sequence: Synthetic
      conserved domain peptide
<220> FEATURE:
<221> NAME/KEY: MOD_RES
<222> LOCATION: (2)..(3)
<223> OTHER INFORMATION: Any amino acid

<400> SEQUENCE: 3

Thr Xaa Xaa Gly Arg
1               5

<210> SEQ ID NO 4
<211> LENGTH: 6
<212> TYPE: PRT
<213> ORGANISM: Artificial Sequence
<220> FEATURE:
<223> OTHER INFORMATION: Description of Artificial Sequence: Synthetic
      conserved domain peptide
<220> FEATURE:
<221> NAME/KEY: MOD_RES
<222> LOCATION: (2)..(2)
<223> OTHER INFORMATION: Any amino acid

<400> SEQUENCE: 4

Tyr Xaa Asp Thr Asp Ser
1               5

<210> SEQ ID NO 5
<211> LENGTH: 3
<212> TYPE: PRT
<213> ORGANISM: Artificial Sequence
<220> FEATURE:
<223> OTHER INFORMATION: Description of Artificial Sequence: Synthetic
      conserved domain peptide
<220> FEATURE:
<221> NAME/KEY: MOD_RES
<222> LOCATION: (2)..(2)
<223> OTHER INFORMATION: Any amino acid

<400> SEQUENCE: 5

Lys Xaa Tyr
1

<210> SEQ ID NO 6
<211> LENGTH: 4
<212> TYPE: PRT
<213> ORGANISM: Artificial Sequence
<220> FEATURE:
<223> OTHER INFORMATION: Description of Artificial Sequence: Synthetic
      conserved domain peptide
<220> FEATURE:
<221> NAME/KEY: MOD_RES
<222> LOCATION: (2)..(2)
<223> OTHER INFORMATION: Any amino acid

<400> SEQUENCE: 6

Tyr Xaa Gly Gly
1

-continued

<210> SEQ ID NO 7
<211> LENGTH: 6
<212> TYPE: PRT
<213> ORGANISM: Artificial Sequence
<220> FEATURE:
<223> OTHER INFORMATION: Description of Artificial Sequence: Synthetic
      conserved domain peptide

<400> SEQUENCE: 7

Ser Tyr Thr Gly Gly Phe
1               5

<210> SEQ ID NO 8
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
gaggagagca ggaaaggtgg aag                                           23

<210> SEQ ID NO 9
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
gaggtacagg gttgaggcta ctg                                           23

<210> SEQ ID NO 10
<211> LENGTH: 776
<212> TYPE: PRT
<213> ORGANISM: Thermococcus sp.

<400> SEQUENCE: 10

Met Ile Leu Asp Val Asp Tyr Ile Thr Glu Asn Gly Lys Pro Val Ile
1               5                   10                  15

Arg Val Phe Lys Lys Glu Asn Gly Glu Phe Arg Ile Glu Tyr Asp Arg
            20                  25                  30

Glu Phe Glu Pro Tyr Phe Tyr Ala Leu Leu Arg Asp Asp Ser Ala Ile
        35                  40                  45

Glu Glu Ile Lys Lys Ile Thr Ala Glu Arg His Gly Arg Val Val Lys
    50                  55                  60

Val Lys Arg Ala Glu Lys Val Lys Lys Phe Leu Gly Arg Ser Val
65                  70                  75                  80

Glu Val Trp Val Leu Tyr Phe Thr His Pro Gln Asp Val Pro Ala Ile
                85                  90                  95

Arg Asp Lys Ile Arg Lys His Pro Ala Val Ile Asp Ile Tyr Glu Tyr
            100                 105                 110

Asp Ile Pro Phe Ala Lys Arg Tyr Leu Ile Asp Lys Gly Leu Ile Pro
        115                 120                 125

Met Glu Gly Glu Glu Glu Leu Lys Leu Met Ser Phe Asp Ile Glu Thr
    130                 135                 140

Leu Tyr His Glu Gly Glu Glu Phe Gly Thr Gly Pro Ile Leu Met Ile
145                 150                 155                 160

Ser Tyr Ala Asp Glu Ser Glu Ala Arg Val Ile Thr Trp Lys Lys Ile

```
                    165                 170                 175
Asp Leu Pro Tyr Val Glu Val Ser Thr Glu Lys Glu Met Ile Lys
                180                 185                 190

Arg Phe Leu Arg Val Val Lys Glu Lys Asp Pro Asp Val Leu Ile Thr
            195                 200                 205

Tyr Asn Gly Asp Asn Phe Asp Phe Ala Tyr Leu Lys Lys Arg Cys Glu
        210                 215                 220

Lys Leu Gly Val Ser Phe Thr Leu Gly Arg Asp Gly Ser Glu Pro Lys
225                 230                 235                 240

Ile Gln Arg Met Gly Asp Arg Phe Ala Val Glu Val Lys Gly Arg Val
                245                 250                 255

His Phe Asp Leu Tyr Pro Val Ile Arg Arg Thr Ile Asn Leu Pro Thr
            260                 265                 270

Tyr Thr Leu Glu Ala Val Tyr Glu Ala Val Phe Gly Lys Pro Lys Glu
        275                 280                 285

Lys Val Tyr Ala Glu Glu Ile Ala Thr Ala Trp Glu Thr Gly Glu Gly
    290                 295                 300

Leu Glu Arg Val Ala Arg Tyr Ser Met Glu Asp Ala Arg Val Thr Tyr
305                 310                 315                 320

Glu Leu Gly Arg Glu Phe Pro Met Glu Ala Gln Leu Ser Arg Leu
                325                 330                 335

Ile Gly Gln Gly Leu Trp Asp Val Ser Arg Ser Ser Thr Gly Asn Leu
            340                 345                 350

Val Glu Trp Phe Leu Leu Arg Lys Ala Tyr Glu Arg Asn Glu Leu Ala
        355                 360                 365

Pro Asn Lys Pro Asp Glu Arg Glu Leu Ala Arg Arg Gly Gly Tyr
    370                 375                 380

Ala Gly Gly Tyr Val Lys Glu Pro Glu Arg Gly Leu Trp Asp Asn Ile
385                 390                 395                 400

Val Tyr Leu Asp Phe Arg Ser Leu Tyr Pro Ser Ile Ile Ile Thr His
                405                 410                 415

Asn Val Ser Pro Asp Thr Leu Asn Arg Glu Gly Cys Arg Ser Tyr Asp
            420                 425                 430

Val Ala Pro Glu Val Gly His Lys Phe Cys Lys Asp Phe Pro Gly Phe
        435                 440                 445

Ile Pro Ser Leu Leu Gly Asn Leu Leu Glu Glu Arg Gln Lys Ile Lys
    450                 455                 460

Arg Lys Met Lys Ala Thr Leu Asp Pro Leu Glu Lys Asn Leu Leu Asp
465                 470                 475                 480

Tyr Arg Gln Arg Ala Ile Lys Ile Leu Ala Asn Ser Tyr Tyr Gly Tyr
                485                 490                 495

Tyr Gly Tyr Ala Arg Ala Arg Trp Tyr Cys Arg Glu Cys Ala Glu Ser
            500                 505                 510

Val Thr Ala Trp Gly Arg Glu Tyr Ile Glu Met Val Ile Arg Glu Leu
        515                 520                 525

Glu Glu Lys Phe Gly Phe Lys Val Leu Tyr Ala Asp Thr Asp Gly Leu
    530                 535                 540

His Ala Thr Ile Pro Gly Ala Asp Ala Glu Thr Val Lys Lys Lys Ala
545                 550                 555                 560

Met Glu Phe Leu Asn Tyr Ile Asn Pro Lys Leu Pro Gly Leu Leu Glu
                565                 570                 575

Leu Glu Tyr Glu Gly Phe Tyr Val Arg Gly Phe Phe Val Thr Lys Lys
            580                 585                 590
```

```
Lys Tyr Ala Val Ile Asp Glu Glu Gly Lys Ile Thr Thr Arg Gly Leu
            595                 600                 605
Glu Ile Val Arg Arg Asp Trp Ser Glu Ile Ala Lys Glu Thr Gln Ala
        610                 615                 620
Arg Val Leu Glu Ala Ile Leu Arg His Gly Asp Val Glu Glu Ala Val
625                 630                 635                 640
Arg Ile Val Arg Glu Val Thr Glu Lys Leu Ser Lys Tyr Glu Val Pro
                645                 650                 655
Pro Glu Lys Leu Val Ile His Glu Gln Ile Thr Arg Glu Leu Lys Asp
            660                 665                 670
Tyr Lys Ala Thr Gly Pro His Val Ala Ile Ala Lys Arg Leu Ala Ala
        675                 680                 685
Arg Gly Val Lys Ile Arg Pro Gly Thr Val Ile Ser Tyr Ile Val Leu
690                 695                 700
Lys Gly Ser Gly Arg Ile Gly Asp Arg Ala Ile Pro Phe Asp Glu Phe
705                 710                 715                 720
Asp Pro Thr Lys His Lys Tyr Asp Ala Asp Tyr Tyr Ile Glu Asn Gln
                725                 730                 735
Val Leu Pro Ala Val Glu Arg Ile Leu Arg Ala Phe Gly Tyr Arg Lys
            740                 745                 750
Glu Asp Leu Arg Tyr Gln Lys Thr Arg Gln Val Gly Leu Gly Ala Trp
        755                 760                 765
Leu Lys Pro Lys Gly Lys Lys Lys
        770                 775

<210> SEQ ID NO 11
<211> LENGTH: 2331
<212> TYPE: DNA
<213> ORGANISM: Thermococcus sp.

<400> SEQUENCE: 11
atgatccttg acgttgatta catcaccgag aatggaaagc ccgtcatcag ggtcttcaag      60
aaggagaacg gcgagttcag gattgaatac gaccgcgagt tcgagcccta cttctacgcg     120
ctcctcaggg acgactctgc catcgaagaa atcaaaaaga taaccgcgga gaggcacggc     180
agggtcgtta aggttaagcg cgcggagaag gtgaagaaaa agttcctcgg caggtctgtg     240
gaggtctggg tcctctactt cacgcacccg caggacgttc cggcaatccg cacaaaaata     300
aggaagcacc ccgcggtcat cgacatctac gagtacgaca taccttcgc caagcgctac      360 ctcatagaca agggcctaat cccgatggaa ggtgaggaag agcttaaact catgtccttc     420
gacatcgaga cgctctacca cgagggagaa gagtttggaa ccgggccgat tctgatgata     480
agctacgccg atgaaagcga ggcgcgcgtg ataacctgga agaagatcga ccttccttac     540
gttgaggttg tctccaccga gaaggagatg attaagcgct tcttgagggt cgttaaggag     600
aaggacccgg acgtgctgat aacatacaac ggcgacaact cgacttcgc ctacctgaaa      660 aagcgctgtg agaagcttgg cgtgagcttt accctcggga gggacgggag cgagccgaag     720
atacagcgca tgggggacag gtttgcggtc gaggtgaagg cagggtaca cttcgacctt      780 tatccagtca taaggcgcac cataaacctc ccgacctaca cccttgaggc tgtatacgag     840
gcggttttcg gcaagcccaa ggagaaggtc tacgccgagg agatagccac cgcctgggag     900
accggcgagg ggcttgagag ggtcgcgcgc tactcgatgg aggacgcgag ggttacctac     960
gagcttggca gggagttctt cccgatggag gcccagcttt ccaggctcat cggccaaggc    1020
```

```
ctctgggacg tttcccgctc cagcaccggc aacctcgtcg agtggttcct cctaaggaag    1080
gcctacgaga ggaacgaact cgctcccaac aagcccgacg agagggagct ggcgaggaga    1140
agggggggct acgccggtgg ctacgtcaag gagccggagc ggggactgtg ggacaatatc    1200
gtgtatctag actttcgtag tctctaccct tcaatcataa tcacccacaa cgtctcgcca    1260
gatacgctca accgcgaggg gtgtaggagc tacgacgttg cccccgaggt cggtcacaag    1320
ttctgcaagg acttccccgg cttcattccg agcctgctcg aaacctgct ggaggaaagg     1380
cagaagataa agaggaagat gaaggcaact ctcgacccgc tggagaagaa tctcctcgat    1440
tacaggcaac gcgccatcaa gattctcgcc aacagctact acggctacta cggctatgcc    1500
agggcaagat ggtactgcag ggagtgcgcc gagagcgtta cggcatgggg aagggagtac    1560
atcgaaatgg tcatcagaga gcttgaggaa aagttcggtt ttaaagtcct ctatgcagac    1620
acagacggtc tccatgccac cattcctgga gcggacgctc aaacagtcaa gaaaaaggca    1680
atggagttct aaactatat caatcccaaa ctgcccggcc ttctcgaact cgaatacgag     1740
ggcttctacg tcagggctt cttcgtcacg aagaaaagt acgcggtcat cgacgaggag      1800
ggcaagataa ccacgcgcgg gcttgagata gtcaggcgcg actggagcga gatagcgaag    1860
gagacgcagg cgagggtttt ggaggcgata ctcaggcacg tgacgttga agaggccgtc     1920
agaattgtca gggaagtcac cgaaaagctg agcaagtacg aggttccgcc ggagaagctg    1980
gttatccacg agcagataac gcgcgagctc aaggactaca aggccaccgg cccgcacgta    2040
gccatagcga agcgtttggc cgccagaggt gttaaaatcc ggcccggaac tgtgataagc    2100
tacatcgttc tgaagggctc cggaaggata ggcgacaggg cgattcccctt cgacgagttc   2160
gacccgacga agcacaagta cgatgcggac tactacatcg agaaccaggt tctgccggca    2220
gttgagagaa tcctcagggc cttcggctac cgcaaggaag acctgcgcta ccagaagacg    2280
aggcaggtcg ggcttggcgc gtggctgaag ccgaagggga agaagaagtg a             2331
```

<210> SEQ ID NO 12
<211> LENGTH: 775
<212> TYPE: PRT
<213> ORGANISM: Pyrococcus furiosus

<400> SEQUENCE: 12

```
Met Ile Leu Asp Val Asp Tyr Ile Thr Glu Glu Gly Lys Pro Val Ile
1               5                   10                  15

Arg Leu Phe Lys Lys Glu Asn Gly Lys Phe Lys Ile Glu His Asp Arg
            20                  25                  30

Thr Phe Arg Pro Tyr Ile Tyr Ala Leu Leu Arg Asp Asp Ser Lys Ile
        35                  40                  45

Glu Glu Val Lys Lys Ile Thr Gly Glu Arg His Gly Lys Ile Val Arg
    50                  55                  60

Ile Val Asp Val Glu Lys Val Glu Lys Lys Phe Leu Gly Lys Pro Ile
65                  70                  75                  80

Thr Val Trp Lys Leu Tyr Leu Glu His Pro Gln Asp Val Pro Thr Ile
                85                  90                  95

Arg Glu Lys Val Arg Glu His Pro Ala Val Val Asp Ile Phe Glu Tyr
            100                 105                 110

Asp Ile Pro Phe Ala Lys Arg Tyr Leu Ile Asp Lys Gly Leu Ile Pro
        115                 120                 125

Met Glu Gly Glu Glu Glu Leu Lys Ile Leu Ala Phe Asp Ile Glu Thr
    130                 135                 140
```

```
Leu Tyr His Glu Gly Glu Glu Phe Gly Lys Gly Pro Ile Ile Met Ile
145                 150                 155                 160

Ser Tyr Ala Asp Glu Asn Glu Ala Lys Val Ile Thr Trp Lys Asn Ile
            165                 170                 175

Asp Leu Pro Tyr Val Glu Val Ser Ser Glu Arg Glu Met Ile Lys
                180                 185                 190

Arg Phe Leu Arg Ile Ile Arg Glu Lys Asp Pro Asp Ile Ile Val Thr
            195                 200                 205

Tyr Asn Gly Asp Ser Phe Asp Phe Pro Tyr Leu Ala Lys Arg Ala Glu
            210                 215                 220

Lys Leu Gly Ile Lys Leu Thr Ile Gly Arg Asp Gly Ser Glu Pro Lys
225                 230                 235                 240

Met Gln Arg Ile Gly Asp Met Thr Ala Val Glu Val Lys Gly Arg Ile
            245                 250                 255

His Phe Asp Leu Tyr His Val Ile Thr Arg Thr Ile Asn Leu Pro Thr
            260                 265                 270

Tyr Thr Leu Glu Ala Val Tyr Glu Ala Ile Phe Gly Lys Pro Lys Glu
            275                 280                 285

Lys Val Tyr Ala Asp Glu Ile Ala Lys Ala Trp Glu Ser Gly Glu Asn
            290                 295                 300

Leu Glu Arg Val Ala Lys Tyr Ser Met Glu Asp Ala Lys Ala Thr Tyr
305                 310                 315                 320

Glu Leu Gly Lys Glu Phe Leu Pro Met Glu Ile Gln Leu Ser Arg Leu
            325                 330                 335

Val Gly Gln Pro Leu Trp Asp Val Ser Arg Ser Ser Thr Gly Asn Leu
            340                 345                 350

Val Glu Trp Phe Leu Leu Arg Lys Ala Tyr Glu Arg Asn Glu Val Ala
            355                 360                 365

Pro Asn Lys Pro Ser Glu Glu Tyr Gln Arg Arg Leu Arg Glu Ser
            370                 375                 380

Tyr Thr Gly Gly Phe Val Lys Glu Pro Glu Lys Gly Leu Trp Glu Asn
385                 390                 395                 400

Ile Val Tyr Leu Asp Phe Arg Ala Leu Tyr Pro Ser Ile Ile Ile Thr
            405                 410                 415

His Asn Val Ser Pro Asp Thr Leu Asn Leu Glu Gly Cys Lys Asn Tyr
            420                 425                 430

Asp Ile Ala Pro Gln Val Gly His Lys Phe Cys Lys Asp Ile Pro Gly
            435                 440                 445

Phe Ile Pro Ser Leu Leu Gly His Leu Leu Glu Glu Arg Gln Lys Ile
            450                 455                 460

Lys Thr Lys Met Lys Glu Thr Gln Asp Pro Ile Glu Lys Ile Leu Leu
465                 470                 475                 480

Asp Tyr Arg Gln Lys Ala Ile Lys Leu Leu Ala Asn Ser Phe Tyr Gly
            485                 490                 495

Tyr Tyr Gly Tyr Ala Lys Ala Arg Trp Tyr Cys Lys Glu Cys Ala Glu
            500                 505                 510

Ser Val Thr Ala Trp Gly Arg Lys Tyr Ile Glu Leu Val Trp Lys Glu
            515                 520                 525

Leu Glu Glu Lys Phe Gly Phe Lys Val Leu Tyr Ile Asp Thr Asp Gly
            530                 535                 540

Leu Tyr Ala Thr Ile Pro Gly Gly Glu Ser Glu Glu Ile Lys Lys Lys
545                 550                 555                 560

Ala Leu Glu Phe Val Lys Tyr Ile Asn Ser Lys Leu Pro Gly Leu Leu
```

-continued

```
                565                    570                    575
Glu Leu Glu Tyr Glu Gly Phe Tyr Lys Arg Gly Phe Phe Val Thr Lys
            580                    585                    590

Lys Arg Tyr Ala Val Ile Asp Glu Glu Gly Lys Val Ile Thr Arg Gly
        595                    600                    605

Leu Glu Ile Val Arg Arg Asp Trp Ser Glu Ile Ala Lys Glu Thr Gln
    610                    615                    620

Ala Arg Val Leu Glu Thr Ile Leu Lys His Gly Asp Val Glu Glu Ala
625                    630                    635                    640

Val Arg Ile Val Lys Glu Val Ile Gln Lys Leu Ala Asn Tyr Glu Ile
                645                    650                    655

Pro Pro Glu Lys Leu Ala Ile Tyr Glu Gln Ile Thr Arg Pro Leu His
            660                    665                    670

Glu Tyr Lys Ala Ile Gly Pro His Val Ala Val Ala Lys Lys Leu Ala
        675                    680                    685

Ala Lys Gly Val Lys Ile Lys Pro Gly Met Val Ile Gly Tyr Ile Val
    690                    695                    700

Leu Arg Gly Asp Gly Pro Ile Ser Asn Arg Ala Ile Leu Ala Glu Glu
705                    710                    715                    720

Tyr Asp Pro Lys Lys His Lys Tyr Asp Ala Glu Tyr Tyr Ile Glu Asn
                725                    730                    735

Gln Val Leu Pro Ala Val Leu Arg Ile Leu Glu Gly Phe Gly Tyr Arg
            740                    745                    750

Lys Glu Asp Leu Arg Tyr Gln Lys Thr Arg Gln Val Gly Leu Thr Ser
        755                    760                    765

Trp Leu Asn Ile Lys Lys Ser
    770                    775
```